US006974823B2

(12) United States Patent
Hamilton

(10) Patent No.: US 6,974,823 B2
(45) Date of Patent: Dec. 13, 2005

(54) HYDANTOIN DERIVATIVE COMPOUNDS, PHARMACEUTICAL COMPOSITIONS, AND METHODS OF USING SAME

(75) Inventor: Gregory S. Hamilton, Catonsville, MD (US)

(73) Assignee: GPI NIL Holdindgs, Inc., Wilmington, DE (US)

( * ) Notice: Subject to any disclaimer, the term of this patent is extended or adjusted under 35 U.S.C. 154(b) by 0 days.

(21) Appl. No.: 09/741,437

(22) Filed: Dec. 21, 2000

(65) Prior Publication Data

US 2002/0058685 A1 May 16, 2002

Related U.S. Application Data

(60) Provisional application No. 60/171,391, filed on Dec. 21, 1999.

(51) Int. Cl.[7] .................. A61K 31/4188; C07D 487/04
(52) U.S. Cl. ..................... 514/307; 514/314; 514/338; 514/365; 514/374; 514/387; 514/388; 546/273.1; 546/152; 546/139; 548/302.7; 548/181; 548/235
(58) Field of Search ........................ 548/302.7, 181, 548/235; 546/273.1, 152, 139; 514/307, 314, 338, 365, 374, 387, 388

(56) References Cited

U.S. PATENT DOCUMENTS

| 2,999,863 | A | | 9/1961 | Upham |
|---|---|---|---|---|
| 3,013,943 | A | | 12/1961 | Berger |
| 3,326,932 | A | | 6/1967 | Kitasaki et al. |
| 3,352,879 | A | | 11/1967 | Finkbeiner |
| 3,389,146 | A | | 6/1968 | Kitasaki et al. |
| 3,847,933 | A | | 11/1974 | Tyler, III |
| 3,864,357 | A | | 2/1975 | Porret et al. |
| 3,920,660 | A | | 11/1975 | Fontanella et al. |
| 3,946,033 | A | | 3/1976 | Iwata et al. |
| 3,948,933 | A | | 4/1976 | Fontanella |
| 3,958,976 | A | | 5/1976 | Goddard |
| 4,138,242 | A | | 2/1979 | Goddard |
| 4,179,276 | A | | 12/1979 | Cheng |
| 4,186,205 | A | * | 1/1980 | Bender ................ 514/393 |
| 4,230,709 | A | | 10/1980 | Jamieson et al. |
| 4,406,689 | A | | 9/1983 | Anderson et al. |
| 4,431,644 | A | | 2/1984 | Smith et al. |
| 4,437,877 | A | | 3/1984 | Nagano et al. |
| 4,531,964 | A | | 7/1985 | Shimano et al. |
| 4,668,683 | A | * | 5/1987 | Takai et al. ........... 514/259 |
| 4,766,110 | A | | 8/1988 | Ryan et al. |
| 4,828,605 | A | | 5/1989 | Haga et al. |
| 5,002,962 | A | | 3/1991 | Loscalzo |
| 5,002,964 | A | | 3/1991 | Loscalzo |
| 5,024,694 | A | | 6/1991 | Schallner et al. |
| 5,049,181 | A | | 9/1991 | Pissiotas et al. |
| 5,053,071 | A | | 10/1991 | Semple |
| 5,069,711 | A | | 12/1991 | Fischer et al. |
| 5,082,838 | A | | 1/1992 | Naka et al. |
| 5,118,849 | A | | 6/1992 | Schallner et al. |
| 5,128,483 | A | | 7/1992 | Trybulski |
| 5,166,317 | A | | 11/1992 | Wallace et al. |
| 5,192,773 | A | | 3/1993 | Armistead et al. |
| 5,214,034 | A | | 5/1993 | Nakayama et al. |
| 5,215,969 | A | | 6/1993 | Springer et al. |
| 5,232,923 | A | | 8/1993 | Fukazawa et al. |
| 5,258,382 | A | | 11/1993 | Negoro et al. |
| 5,321,009 | A | | 6/1994 | Baeder et al. |
| 5,330,993 | A | | 7/1994 | Armistead et al. |
| 5,338,859 | A | | 8/1994 | Bhattacharya |
| 5,342,942 | A | | 8/1994 | Jaen et al. |
| 5,359,138 | A | | 10/1994 | Takeuchi et al. |
| 5,453,437 | A | | 9/1995 | Schohe et al. |
| 5,482,921 | A | | 1/1996 | Seckinger et al. |
| 5,504,197 | A | | 4/1996 | Schubert et al. |
| 5,506,243 | A | | 4/1996 | Ando et al. |
| 5,516,797 | A | | 5/1996 | Armistead et al. |

(Continued)

FOREIGN PATENT DOCUMENTS

| DE | 3636278 | | 10/1986 |
|---|---|---|---|
| DE | 197 42 263 | | 9/1997 |
| EP | 405994 | | 1/1991 |
| EP | 443983 | | 8/1991 |
| EP | 476933 | | 3/1992 |
| EP | 488 258 | | 6/1992 |
| EP | 805 147 | | 11/1997 |
| GB | 1503244 | A * | 3/1978 |
| JP | 5283686 | A2 * | 7/1977 |
| WO | WO 88/09789 | | 12/1988 |
| WO | WO 92/00278 | | 1/1992 |
| WO | WO 92/04370 | | 3/1992 |

OTHER PUBLICATIONS

US 5,654,332, 8/1997, Armistead (withdrawn)
An English translation of WO 96/06846, Mar. 7, 1996.*
An English translation of JP 52–083686, Jul. 12, 1977.*
Kunz, Chemical Abstracts, vol. 1999: 672790 ZCAPLUS, 1999.
Moloney, Chemical Abstracts, vol. 131:170303, 1999.
Boynton, Chemical Abstracts, vol. 129:119080, 1998.
Lopez–Rodriguez, Chemical Abstracts, vol. 126:271825, 1997.
Lopez Rodriguez, Chemical Abstracts, vol. 125:86677, 1996.

(Continued)

*Primary Examiner*—Laura L. Stockton
(74) *Attorney, Agent, or Firm*—Foley & Lardner LLP

(57) ABSTRACT

The present invention relates generally to novel hydantoin derivative compounds, pharmaceutical compositions containing such compounds, and methods for their use in preventing and/or treating neurological disorders, including physically damaged nerves and neurodegenerative diseases; for treating alopecia and promoting hair growth; for treating vision disorders and/or improving vision; for treating memory impairment and/or enhancing memory performance; and for treating sensorineural hearing loss by administering such compounds.

3 Claims, No Drawings

U.S. PATENT DOCUMENTS

| | | |
|---|---|---|
| 5,527,907 A | 6/1996 | Or et al. |
| 5,536,737 A | 7/1996 | Kobayashi et al. |
| 5,541,189 A | 7/1996 | Luly et al. |
| 5,543,423 A | 8/1996 | Zelle et al. |
| 5,605,877 A | 2/1997 | Schafer et al. |
| 5,614,547 A | 3/1997 | Hamilton et al. |
| 5,620,971 A | 4/1997 | Armistead et al. |
| 5,629,325 A | 5/1997 | Lin et al. |
| 5,665,681 A | 9/1997 | Seckinger et al. |
| 5,665,774 A | 9/1997 | Armistead et al. |
| 5,696,135 A | 12/1997 | Steiner et al. |
| 5,703,088 A | 12/1997 | Sharpe et al. |
| 5,714,437 A | 2/1998 | Takano et al. |
| 5,714,510 A | 2/1998 | Proctor |
| 5,717,092 A | 2/1998 | Armistead et al. |
| 5,721,256 A | 2/1998 | Hamilton et al. |
| 5,744,485 A | 4/1998 | Zelle et al. |
| 5,780,484 A | 7/1998 | Zelle et al. |
| 5,783,707 A | 7/1998 | Elokdah et al. |
| 5,786,378 A | 7/1998 | Hamilton et al. |
| 5,795,908 A | 8/1998 | Hamilton et al. |
| 5,798,355 A | 8/1998 | Steiner et al. |
| 5,801,187 A | 9/1998 | Li et al. |
| 5,801,197 A | 9/1998 | Steiner et al. |
| 5,811,434 A | 9/1998 | Zelle |
| 5,840,736 A | 11/1998 | Zelle |
| 5,843,960 A | 12/1998 | Steiner et al. |
| 5,846,979 A | 12/1998 | Hamilton et al. |
| 5,846,981 A | 12/1998 | Steiner et al. |
| 5,859,031 A | 1/1999 | Hamilton et al. |
| 5,874,449 A | 2/1999 | Hamilton et al. |
| 5,898,029 A | 4/1999 | Lyons et al. |
| 5,935,989 A | 8/1999 | Hamilton et al. |
| 5,958,949 A | 9/1999 | Hamilton et al. |
| 5,968,957 A | 10/1999 | Hamilton et al. |
| 5,990,131 A | 11/1999 | Hamilton et al. |
| 6,022,878 A | 2/2000 | Steiner et al. |
| 6,037,370 A | 3/2000 | Armistead |
| 6,054,452 A | 4/2000 | Hamilton et al. |

FOREIGN PATENT DOCUMENTS

| | | |
|---|---|---|
| WO | WO 92/11245 | 7/1992 |
| WO | WO 92/11850 | 7/1992 |
| WO | WO 92/19593 | 11/1992 |
| WO | WO 92/21313 | 12/1992 |
| WO | WO 93/13066 | 7/1993 |
| WO | WO 93/14072 | 7/1993 |
| WO | WO 94/12474 | 6/1994 |
| WO | WO 94/15900 | 7/1994 |
| WO | WO 95/35308 | 12/1995 |
| WO | WO 95/35367 | 12/1995 |
| WO | WO 96/06846 | 3/1996 |
| WO | WO 96/20725 | 11/1996 |
| WO | WO 96/20949 | 11/1996 |
| WO | WO 96/40140 | 12/1996 |
| WO | WO 96/40633 | 12/1996 |
| WO | WO 96/41609 | 12/1996 |
| WO | WO 97/23202 | 3/1997 |
| WO | WO 97/23458 | 3/1997 |
| WO | WO 97/36869 | 9/1997 |
| WO | WO 97/38008 | 10/1997 |
| WO | WO 97/20554 | 12/1997 |
| WO | WO 97/48681 | 12/1997 |
| WO | WO 97/49695 | 12/1997 |
| WO | WO 98/13343 | 2/1998 |
| WO | WO 98/08814 | 3/1998 |
| WO | WO 98/08827 | 3/1998 |
| WO | WO 98/37885 | 3/1998 |
| WO | WO 98/20891 | 5/1998 |
| WO | WO 98/20892 | 5/1998 |
| WO | WO 98/20893 | 5/1998 |
| WO | WO 98/29117 | 9/1998 |
| WO | WO 98/55091 | 10/1998 |
| WO | WO 98/24805 | 11/1998 |
| WO | WO 99/10340 | 3/1999 |

OTHER PUBLICATIONS

Lopez–Rodriguez, Chemical Abstracts, vol. 125:238292, 1996.
Lopez–Rodriguez, Chemical Abstracts, vol. 124:306509, 1996.
Lepri, Chemical Abstracts, vol. 124:277362, 1996.
Ganzer, Chemical Abstracts, vol. 120:164204, 1994.
Sano, Chemical Abstracts, vol. 119:139210, 1993.
Sato, Chemical Abstracts, vol. 119:175791, 1993.
Sato, Chemical Abstracts, vol. 117:145248, 1992.
Ganzer, Chemical Abstracts, vol. 114:143432, 1991.
Ganzer, Chemical Abstracts, vol. 111:174127, 1989.
Kume, Chemical Abstracts, vol. 89:10618, 1989.
Kume, Chemical Abstracts, vol. 109:73459, 1988.
Kyowa, Chemical Abstracts, vol. 98:198237, 1983.
Ohta, Chemical Abstracts, vol. 94:133973, 1981.
Wakabayashi, Chemical Abstracts, vol. 91:169807, 1979.
Mitsubishi, Chemical Abstracts, vol. 93:46672, 1980.
Schon, Chemical Abstracts, vol. 90:187304, 1979.
Wakabayashi, Chemical Abstracts, vol. 88:22905, 1978.
Wakabayashi, Chemical Abstracts, vol. 85:160100, 1976.
Sinsheimer, Chemical Abstracts, vol. 83:163972, 1975.
Sam, Chemical Abstracts, vol. 72:3429, 1970.
Imbach, Chemical Abstracts, vol. 60:2923b CAOLD, 1964.
Wistuba, Chemical Abstracts, vol. 129:197341, 1998.
Bhatnagar, Chemical Abstracts, vol. 127:50659, 1997.
Grosenick, Chemical Abstracts, vol. 126:338170, 1997.
Chen, Chemical Abstracts, vol. 126:220124, 1997.
Schurig, Chemical Abstracts, vol. 126:112546, 1996.
Murray, Chemical Abstracts, vol. 122:187833, 1995.
Yohannes, Chemical Abstracts, vol. 118:147360, 1993.
Lepri, Chemical Abstracts, vol. 118:72825, 1993.
Fisher, Chemical Abstracts, vol. 114:228608, 1991.
Guenoun, Chemical Abstracts, vol. 113:172716, 1990.
Dunkerton, Chemical Abstracts, vol. 110:58063, 1989.
Sleeckx, Chemical Abstracts, vol. 112:21262, 1990.
Kammueller, Chemical Abstracts, vol. 110:87992, 1989.
Huff, Chemical Abstracts, vol. 108:94365, 1988.
Lunkenheimer, Chemical Abstracts, vol. 107:91913, 1987.
Boykin, Chemical Abstracts, vol. 108:37078, 1988.
Nakatsuka, Chemical Abstracts, vol. 107:197891, 1987.
Nakatsuka, Chemical Abstracts, vol. 106:196663, 1987.
Reyniers, Chemical Abstracts, vol. 104:149387, 1986.
Thiel, Chemical Abstracts, vol. 104:88496, 1986.
Liao, Chemical Abstracts, vol. 102:6312, 1985.
Shukla, Chemical Abstracts, vol. 100:34500, 1984.
Kessler, Chemical Abstracts, vol. 98:161158, 1983.
Anteunis, Chemical Abstracts, vol. 96:69397, 1982.
Thiel, Chemical Abstracts, vol. 99:5590, 1983.
Jamieson, Chemical Abstracts, vol. 94:103378, 1981.
Cung, Chemical Abstracts, vol. 93:95651, 1980.
Smail, Chemical Abstracts, vol. 94:167458, 1981.
Horn, Chemical Abstracts, vol. 92:193679, 1980.
Siemion, Chemical Abstracts, vol. 91:38801, 1979.
Fuzuki, Chemical Abstracts, vol. 87:168372, 1977.
Liberek, Chemical Abstracts, vol. 88:191390, 1978.
Yamada, Chemical Abstracts, vol. 84:161456, 1976.
Liberek, Chemical Abstracts, vol. 84:180607, 1976.

Volodin, Chemical Abstracts, vol. 86:1005, 1977.
Rothe, Chemical Abstracts, vol. 81:63967, 1974.
Nowak, Chemical Abstracts, vol. 80:142755, 1974.
Arata, Chemical Abstracts, vol. 79:78765, 1973.
Mauger, Chemical Abstracts, vol. 77:102227, 1972.
Crabb, Chemical Abstracts, vol. 77:151363, 1972.
Sun, Chemical Abstracts, vol. 76:32002, 1972.
Rothe, Chemical Abstracts, vol. 85:143469, 1976.
Sun, Chemical Abstracts, vol. 76:72760, 1972.
Oshiro, Chemical Abstracts, vol. 75:49087, 1971.
Mauger, Chemical Abstracts, vol. 75:36647, 1971.
Toniolo, Chemical Abstracts, vol. 74:60936, 1971.
Capuano, Chemical Abstracts, vol. 73:77186, 1970.
Likhosherstov, Chemical Abstracts, vol. 73:109724, 1970.
Tschesche, Chemical Abstracts, vol. 74:54160, 1971.
Winterfeld, Chemical Abstracts, vol. 74:3456, 1971.
Attrill, Chemical Abstracts, vol. 72:133164, 1970.
Campbell, Chemical Abstracts, vol. 71:112884, 1969.
Richards, Chemical Abstracts, vol. 71:30677, 1969.
Okamoto, Chemical Abstracts, vol. 73:88146, 1970.
Mauger, Chemical Abstracts, vol. 70:16866, 1969.
Beyerman, Chemical Abstracts, vol. 68:95759, 1968.
Stepanov, Chemical Abstracts, vol. 64:14262e CAOLD, 1966.
Krivtsov, Chemical Abstracts, vol. 63:669f CAOLD, 1965.
Freed, Chemical Abstracts, vol. 55:10444h CAOLD, 1961.
Elmore, Chemical Abstracts, vol. 53:6215a CAOLD, 1959.
Leonard, Chemical Abstracts, vol. 51:1172g CAOLD, 1957.
Pulman, Chemical Abstracts, vol. 129:256468, 1998.
Hirai, Chemical Abstracts, vol. 128:217380, 1998.
Crews, Chemical Abstracts, vol. 128:217387, 1998.
Gengenbach, Chemical Abstracts, vol. 128:227075, 1998.
Bertram, Chemical Abstracts, vol. 129:256472, 1998.
Liu, Chemical Abstracts, vol. 129:89635, 1998.
Adams, Chemical Abstracts, vol. 127:17676, 1997.
Huber, Chemical Abstracts, vol. 127:274805, 1997.
Baures, Chemical Abstracts, vol. 127:303205, 1997.
Zhou, Chemical Abstracts, vol. 127:356642, 1997.
De Luca, Chemical Abstracts, vol. 128:123431, 1997.
Uraguchi, Chemical Abstracts, vol. 128:58546, 1997.
Duggan, Chemical Abstracts, vol. 125:276449, 1996.
Ott, Chemical Abstracts, vol. 126:1416, 1996.
Kamireddy, Chemical Abstracts, vol. 124:232492, 1996.
Linker, Chemical Abstracts, vol. 124:176141, 1996.
Drewes, Chemical Abstracts, vol. 124:145896, 1995.
Linker, Chemical Abstracts, vol. 124:202276, 1996.
Ramsay, Chemical Abstracts, vol. 124:176843, 1995.
Li, Chemical Abstracts, vol. 124:250548, 1996.
Ganzer, Chemical Abstracts, vol. 122:31576, 1995.
Mach, Chemical Abstracts, vol. 122:3566, 1995.
Baures, Chemical Abstracts, vol. 121:231353, 1994.
Yamada, Chemical Abstracts, vol. 121:9089, 1994.
Bhushan, Chemical Abstracts, vol. 120:293258, 1994.
Natsume, Chemical Abstracts, vol. 120:270091, 1994.
Johann, Chemical Abstracts, vol. 119:88917, 1993.
Zhao, Chemical Abstracts, vol. 118:115937, 1993.
Fields, Chemical Abstracts, vol. 119:203799, 1993.
Seckinger, Chemical Abstracts, vol. 118:6973, 1993.
Pissiotas, Chemical Abstracts, vol. 116:214522, 1992.
Ganzer, Chemical Abstracts, vol. 118:101946, 1993.
Waldron, Chemical Abstracts, vol. 117:419595, 1992.
Fields, Chemical Abstracts, vol. 117:70274, 1992.
Wu, Chemical Abstracts, vol. 116:207099, 1992.
Watanabe, Chemical Abstracts, vol. 116:250334, 1992.
Mustafa, Chemical Abstracts, vol. 118:93532, 1993.
Pavlik, Chemical Abstracts, vol. 116:147464, 1992.
Bertram, Chemical Abstracts, vol. 115:207850, 1991.
Babczinski, Chemical Abstracts, vol. 116:101022, 1992.
Uchiyama, Chemical Abstracts, vol. 115:251588, 1991.
Zhou, Chemical Abstracts, vol. 117:124304, 1992.
Iskierko, Chemical Abstracts, vol. 118:204429, 1993.
Kunisch, Chemical Abstracts, vol. 114:164000, 1991.
Onodera, Chemical Abstracts, vol. 114:101993, 1991.
Kume, Chemical Abstracts, vol. 113:211999, 1990.
Pissiotas, Chemical Abstracts, vol. 113:211972, 1990.
Fischer, Chemical Abstracts, vol. 113:172017, 1990.
Fischer, Chemical Abstracts, vol. 113:23688, 1990.
Waldron, Chemical Abstracts, vol. 114:20542, 1991.
Persson, Chemical Abstracts, vol. 114:77996, 1991.
Wang, Chemical Abstracts, vol. 114:35175, 1991.
Semple, Chemical Abstracts, vol. 113:6148, 1990.
Van Wauwe, Chemical Abstracts, vol. 112:77226, 1990.
Pissiotas, Chemical Abstracts, vol. 113:6337, 1990.
Schallner, Chemical Abstracts, vol. 113:6153, 1990.
Pavlik, Chemical Abstracts, vol. 112:179770, 1990.
Salva, Chemical Abstracts, vol. 111:170338, 1989.
Tempst, Chemical Abstracts, vol. 112:32794, 1990.
Xu, Chemical Abstracts, vol. 112:48249, 1990.
Hayakawa, Chemical Abstracts, vol. 110:208676, 1989.
Stocchi, Chemical Abstracts, vol. 111:3500, 1989.
Fischer, Chemical Abstracts, vol. 111:53518, 1989.
Bhushan, Chemical Abstracts, vol. 110:188653, 1989.
Hagiwara, Chemical Abstracts, vol. 119:203393, 1993.
Kume, Chemical Abstracts, vol. 110:173245, 1989.
Semple, Chemical Abstracts, vol. 109:190245, 1988.
Blume, Chemical Abstracts, vol. 109:129025, 1988.
Golebiewski, Chemical Abstracts, vol. 109:226771, 1988.
Bhushan, Chemical Abstracts, vol. 109:89070, 1988.
McClung, Chemical Abstracts, vol. 109:69689, 1988.
Chan, Chemical Abstracts, vol. 110:91482, 1989.
Ashraf–Khorassani, Chemical Abstracts, vol. 110:3919, 1989.
Pramanik, Chemical Abstracts, vol. 110:54076, 1989.
Le Caer, Chemical Abstracts, vol. 108:127806, 1988.
Xu, Chemical Abstracts, vol. 111:233511, 1989.
Haga, Chemical Abstracts, vol. 107:217620, 1987.
Haga, Chemical Abstracts, vol. 108:94578, 1988.
Liebl, Chemical Abstracts, vol. 108:6018, 1988.
Engelke, Chemical Abstracts, vol. 106:95341, 1987.
Bhushan, Chemical Abstracts, vol. 107:3517, 1987.
Okamoto, Chemical Abstracts, vol. 107:73582, 1987.
Naohara, Chemical Abstracts, vol. 106:18567, 1987.
Matsumoto, Chemical Abstracts, vol. 104:207295, 1986.
Matsumoto, Chemical Abstracts, vol. 105:60524, 1986.
Johansson, Chemical Abstracts, vol. 105:2954, 1986.
Matsumoto, Chemical Abstracts, vol. 107:198894, 1987.
Unger, Chemical Abstracts, vol. 105:3032, 1986.
Lee, Chemical Abstracts, vol. 105:6639, 1986.
Okada, Chemical Abstracts, vol. 104:168469, 1986.
Mitsubishi, Chemical Abstracts, vol. 103:141961, 1985.
Mitsubishi, Chemical Abstracts, vol. 103:196091, 1985.
Clark, Chemical Abstracts, vol. 104:50787, 1986.
Lee, Chemical Abstracts, vol. 103:37612, 1985.
Lottspeich, Chemical Abstracts, vol. 103:119116, 1985.
Simmaco, Chemical Abstracts, vol. 104:149373, 1986.
Stocchi, Chemical Abstracts, vol. 105:79317, 1986.
Games, Chemical Abstracts, vol. 103:67797, 1985.
Shimano, Chemical Abstracts, vol. 101:110916, 1984.

Fater, Chemical Abstracts, vol. 101:187204, 1984.
Bhushan, Chemical Abstracts, vol. 102:162426, 1985.
Cohen, Chemical Abstracts, vol. 102:109135, 1985.
Mahachi, Chemical Abstracts, vol. 102:92308, 1985.
Takeuchi, Chemical Abstracts, vol. 100:202802, 1984.
Anderson, Chemical Abstracts, vol. 100:6517, 1984.
Mitsubishi, Chemical Abstracts, vol. 100:103378, 1984.
Drauz, Chemical Abstracts, vol. 99:38810, 1983.
Nagano, Chemical Abstracts, vol. 99:5630, 1983.
Fairwell, Chemical Abstracts, vol. 99:49835, 1983.
Pucci, Chemical Abstracts, vol. 100:31688, 1984.
Sumitomo, Chemical Abstracts, vol. 98:126090, 1983.
Mancheva, Chemical Abstracts, vol. 99:47326, 1983.
Mammo, Chemical Abstracts, vol. 99:16091, 1983.
Kent, Chemical Abstracts, vol. 99:22893, 1983.
Chen, Chemical Abstracts, vol. 96:200120, 1982.
Bledsoe, Chemical Abstracts, vol. 96:200123, 1982.
Margolies, Chemical Abstracts, vol. 97:24199, 1982.
DiMari, Chemical Abstracts, vol. 95:143588, 1981.
Kinoshita, Chemical Abstracts, vol. 93:91531, 1980.
Lottspeich, Chemical Abstracts, vol. 95:2770, 1981.
Goddard, Chemical Abstracts, vol. 91:39478, 1979.
Moser, Chemical Abstracts, vol. 92:2596, 1980.
Poupaert, Chemical Abstracts, vol. 92:76398, 1980.
Datta, Chemical Abstracts, vol. 90:182514, 1979.
Horn, Chemical Abstracts, vol. 92:193679, 1980.
Hisada, Chemical Abstracts, vol. 89:43410, 1978.
Hunkapiller, Chemical Abstracts, vol. 89:102945, 1978.
Fong, Chemical Abstracts, vol. 89:38885, 1978.
Bhown, Chemical Abstracts, vol. 88:148364, 1978.
Munier, Chemical Abstracts, vol. 89:110312, 1978.
Margolies, Chemical Abstracts, vol. 88:185497, 1978.
Hauesler, Chemical Abstracts, vol. 88:136967, 1978.
Lu, chemical Abstracts, vol. 90:204450, 1979.
Abrahamsson, Chemical Abstracts, vol. 89:129906, 1978.
Mancheva, Chemical Abstracts, vol. 89:180316, 1978.
Oestvold, Chemical Abstracts, vol. 90:50760, 1979.
Zeeuws, Chemical Abstracts, vol. 88:117175, 1978.
Raulais, Chemical Abstracts, vol. 89:24767, 1978.
Fong, Chemical Abstracts, vol. 88:2537, 1978.
Nazimov, Chemical Abstracts, vol. 86:117067, 1977.
Appella, Chemical Abstracts, vol. 89:102932, 1978.
Goddard, Chemical Abstracts, vol. 85:123923, 1976.
Schneider, Chemical Abstracts, vol. 86:1910, 1977.
Ohta, Chemical Abstracts, vol. 85:42085, 1976.
Tsai, Chemical Abstracts, vol. 84:56100, 1976.
Sinsheimer, Chemical Abstracts, vol. 83:163972, 1975.
Marshall, Chemical Abstracts, vol. 82:121782, 1975.
Iskierko, Chemical Abstracts, vol. 83:97878, 1975.
Oshiro, Chemical Abstracts, vol. 78:147966, 1973.
Oshiro, Chemical Abstracts, vol. 78:147963, 1973.
Ivanov, Chemical Abstracts, vol. 79:1613, 1973.
Guha, Chemical Abstracts, vol. 81:74294, 1974.
Inglis, Chemical Abstracts, vol. 80:37435, 1974.
Klimek, Chemical Abstracts, vol. 80:83586, 1974.
Inglis, Chemical Abstracts, vol. 76:82428, 1972.
Kawauchi, Chemical Abstracts, vol. 75:20961, 1971.
Hagenmaier, Chemical Abstracts, vol. 73:106188, 1970.
Auterhoff, Chemical Abstracts, vol. 73:131280, 1970.
Hoffman–La Roche, Chemical Abstracts, vol. 69:59272, 1968.
Van Hes, Chemical Abstracts, vol. 68:105419, 1968.
Chemical Abstracts, vol. 60:13546f CAOLD, 1964.
Chemical Abstracts, vol. 56:14241d CAOLD, 1962.

Gudasheva, T.A. et al., "Synthesis and antiamnesic activity of a series of N–acylprolyl–containing dipeptides," Eur. J. Med. Chem., 1996, 31, 151–157.
Dawson, T. et al., "Immunosuppressant FK506 enhances phosphorylation of nitric oxide synthase and protects against glutamate neurotoxicity," Proc. Natl. Acad. Sci. USA, 1993, 90, 9808–9812.
Dawson, T. et al., "The immunophilins, FK506 binding protein and cyclophilin, are discretely localized in the brain: relationship to calcineurin," Neuroscience, 1994, 62, 569–580.
Gold, B. et al., "Regulation of the Transcription Factor c–JUN by nerve growth factor in adult sensory neurons," Neuroscience Letters, 1993, 154, 129–133.
Gold, B. et al., "Regulation of aberrant neurofilament phosphorylation in neuronal perikarya. IV. Evidence for the involvement of two signals," Brain Research, 1993, 626, 23–30.
Gold, B. et al., "The immunosuppressant FK506 increases functional recovery and nerve regeneration following peripheral nerve injury," Restorative Neurology and Neuroscience, 1994, 6, 287–296.
Gold, B. et al., "Multiple signals underlie the axotomy–induced up–regulation of c–JUN in adult sensory neurons," Neuroscience Letters, 1994, 176, 123–127.
Gold, B. et al., "The immunosuppressant FK506 increases the rate of axonal regeneration in rat sciatic nerves," J. Neuroscience, 1995, 15, 7509–7516.
Hamilton, G. et al., "Neuroimmunophilin Ligands as Novel Therapeutics for the Treatment of Degenerative Disorders of the Nervous System," 1–71, year not available.
Kitamura et al., "Suppressive Effect of FK–506, a Novel Immunosuppressant, Against MPTP–Induced Dopamine Depletion in the Striatum of Young C57BL/6 Mice," J. Neuroimmunology, 1994, 50, 221–224.
Lyons, W. E. et al., "Immunosuppressant FK506 promotes neurite outgrowth in cultures of PC 12 cells and sensory ganglia," Proc. Natl. Acad. Sci. USA, 1994, 91, 3191–3195.
Lyons, W. E. et al., "Neuronal Regeneration Enhances the Expression of the Immunophilin FKBP–12," J. Neuroscience, 1995, 15(4), 2985–2994.
Ryba et al., "Cyclosporine A Prevents Neurological Deterioration of Patients with SAH—A Preliminary Report," Acta Neurochirurgica, 1991, 112, 25–27.
Shiga et al., "Cyclosporin A Protects Against Ischemia–Reperfusion Injury in the Brain," Brain Research, 1992, 595, 145–148.
Snyder, S. et al., "Immunophilins and the Nervous System", Nature Medicine, 1995, 1, 32–37.
Steiner, J. et al., "High brain densities of the immunophilin FKBP colocalized with calcineurin," Nature, 1992, 358, 584–587.
Steiner, J. et al., "Nonimmunosuppressive ligands for neuroimmunophilins promote nerve extension in vitro and in vivo," Society for Neuroscience Abstracts, 1996, 22, 297.13.
Steiner, J. et al., "Neurotrophic immunophilin ligands stimulate structural and functional recovery in neurodegenerative animal models," Proc. Natl. Acad. Sci. USA, 1997, 94, 2019–2024.
Steiner, J. et al., "Neurotrophic actions of nonimmunosuppressive analogues of immunosuppressive drugs FK506, rapamycin and cyclosporin A," Nature Medicine, 1997, 421–428.

Teichner et al., "Treatment with Cyclosporine A Promotes Axonal Regeneration in Rats Submitted to Transverse Section of the Spinal Cord," *Int'l. J. Brain Research & Neurobio.*, 1993, 34(3), 343–349.

Kozikowski, A.P. et al., "Alzheimer's Therapy: An Approach to Novel Muscarinic Ligands Based Upon the Naturally Occurring Alkaloid Himbacine," *Bioorg & Med. Chem. Lett.*, 1992, 2, 797–802.

Nicolaides, E.D. et al., "Modified Di– and Tripeptides of the C–Terminal Portion of Oxytocin and Vasopressin as Possible Cognition Activation Agents," *J. Med. Chem.*, 1986, 29, 959–971.

DeRuiter, Jack et al., "In Vitro Aldose Reductase Inhibitory Activity of Substituted N–Benzenesulfonylglycine Derivatives," *J. Pharm. Sci.*, 1987, 76(2), 149–152.

Caufield, C. et al., "Macrocyclic Immunomodulators," *Ann. Rep. Med. Chem.*, 1989, 195–204.

* cited by examiner

HYDANTOIN DERIVATIVE COMPOUNDS, PHARMACEUTICAL COMPOSITIONS, AND METHODS OF USING SAME

This application claims benefit of application Ser. No. 60/171,391 filed Dec. 21, 1999.

BACKGROUND OF THE INVENTION

1. Field of Invention

This invention relates to novel hydantoin and hydantoin derivative compounds, their inclusion in pharmaceutical compositions, and their preparation and use for preventing and/or treating neurological disorders; for treating alopecia and promoting hair growth; for treating vision disorders and/or improving vision; for treating memory impairment and/or enhancing memory performance; and for preventing and/or treating hearing loss in an animal.

2. Description of Related Art

It has been found that picomolar concentrations of an immunosuppressant such as FK506 and rapamycin stimulate neurite outgrowth in PC12 cells and sensory nervous, namely dorsal root ganglion cells (DRGs). Lyons et al., *Proc. Of Natl. Acad. Sci.,* 1994 vol. 91, pp. 3191–3195. In whole animal experiments, FK506 has been shown to stimulate nerve regeneration following facial nerve injury and results in functional recovery in animals with sciatic nerve lesions.

Several neurotrophic factors effecting specific neuronal populations in the central nervous system have been identified. For example, it has been hypothesized that Alzheimer's disease results from a decrease or loss of nerve growth factor (NGF). It has thus been proposed to treat Alzheimer's patients with exogenous nerve growth factor or other neurotrophic proteins such as brain derived nerve factor (BDNF), glial derived nerve factor, ciliary neurotrophic factor, and neurotropin-3 to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressants exhibit a number of potentially serious side effects including nephrotoxicity, such as impairment of glomerular filtration and irreversible interstitial fibrosis (Kopp et al., 1991, *J. Am. Soc. Nephrol.* 1:162); neurological deficits, such as involuntary tremors, or non-specific cerebral angina such as non-localized headaches (De Groen et al., 1987, *N. Engl. J. Med.* 317:861); and vascular hypertension with complications resulting therefrom (Kahan et al., 1989 *N. Engl. J. Med.* 321:1725).

Accordingly, there is a need for non-immunosuppressive, small-molecule compounds which are useful for neurotrophic effects and for treating neurodegenerative disorders.

Hair loss occurs in a variety of situations. These situations include male pattern alopecia, alopecia senilis, alopecia areata, diseases accompanied by basic skin lesions or tumors, and systematic disorders such as nutritional disorders and internal secretion disorders. The mechanisms causing hair loss are very complicated, but in some instances can be attributed to aging, genetic disposition, the activation of male hormones, the loss of blood supply to hair follicles, and scalp abnormalities.

The immunosuppressant drugs FK506, rapamycin and cyclosporin are well known as potent T-cell specific immunosuppressants, and are effective against graft rejection after organ transplantation. It has been reported that topical, but not oral, application of FK506 (Yamamoto et al., *J. Invest. Dermatol.,* 1994, 102, 160–164; Jiang et al., *J. Invest. Dermatol.* 1995, 104, 523–525) and cyclosporin (Iwabuchi et al., *J. Dermatol. Sci.* 1995, 9, 64–69) stimulates hair growth in a dose-dependent manner. One form of hair loss, alopecia areata, is known to be associated with autoimmune activities; hence, topically administered immunomodulatory compounds are expected to demonstrate efficacy for treating that type of hair loss. The hair growth stimulating effects of FK506 have been the subject of an international patent filing covering FK506 and structures related thereto for hair growth stimulation (Honbo et al., EP 0 423 714 A2). Honbo et al. discloses the use of relatively large tricyclic compounds, known for their immunosuppressive effects, as hair revitalizing agents.

The hair growth and revitalization effects of FK506 and related agents are disclosed in many U.S. patents (Goulet et al., U.S. Pat. No. 5,258,389; Luly et al., U.S. Pat. No. 5,457,111; Goulet et al., U.S. Pat. No. 5,532,248; Goulet et al., U.S. Pat. No. 5,189,042; and Ok et al., U.S. Pat. No. 5,208,241; Rupprecht et al., U.S. Pat. No. 5,284,840; Organ et al., U.S. Pat. No. 5,284,877). These patents claim FK506 related compounds. Although they do not claim methods of hair revitalization, they disclose the known use of FK506 for effecting hair growth. Similar to FK506 (and the claimed variations in the Honbo et al. patent), the compounds claimed in these patents are relatively large. Further, the cited patents relate to immunomodulatory compounds for use in autoimmune related diseases, for which FK506's efficacy is well known.

Other U.S. patents disclose the use of cyclosporin and related compounds for hair revitalization (Hauer et al., U.S. Pat. No. 5,342,625; Eberle, U.S. Pat. No. 5,284,826; Hewitt et al., U.S. Pat. No. 4,996,193). These patents also relate to compounds useful for treating autoimmune diseases and cite the known use of cyclosporin and related immunosuppressive compounds for hair growth.

However, immunosuppressive compounds by definition suppress the immune system and also exhibit other toxic side effects. Accordingly, there is a need for non-immunosuppressive, small molecule compounds which are useful as hair revitalizing compounds.

The visual system is composed of the eyes, ocular adnexa and the visual pathways. Dysfunction of the visual system may lead to permanent or temporary visual impairment, i.e. a deviation from normal in one or more functions of the eye. Visual impairment manifests itself in various ways and includes a broad range of visual dysfunctions and disturbances. Without limitation, these dysfunctions and disturbances include partial or total loss of vision, the need for correction of visual acuity for objects near and far, loss of visual field, impaired ocular motility without diplopia (double vision), impaired or skewed color perception, limited adaptation to light and dark, diminished accommodation, metamorphopsic distortion, impaired binocular vision, paresis of accommodation, iridoplegia, entropion, ectropion, epiphora, lagophthalmos, and scarring. See *Physicians' Desk Reference (PDR) for Ophthalmology,* 16th Edition, 6:47 (1988). The visual system may be adversely affected by various ophthalmologic disorders, diseases, injuries, and complications, including, without limitation, genetic disorders; disorders associated with aging or degenerative diseases; disorders correlating to physical injury to the eye, head, or other parts of the body resulting from external forces; disorders resulting from environmental factors; disorders resulting from a broad range of diseases; and combinations of any of the above.

The visual system is a complex system composed of numerous components. Visual impairment can involve the entire visual system, any one component, or any combination of components, depending upon the precise nature of the circumstances. The eye is composed of a lens, which is suspended in the zonules of Zinn and is focused by the ciliary body. The ciliary body also secretes aqueous humor, which fills the posterior chamber, passes through the pupil into the anterior chamber, then drains primarily via the canal of Schlemm. The iris regulates the quantity of light entering the eye by adjusting the size of its central opening, the pupil. A visual image is focused onto the retina, the fovea centralis being the retinal area of sharpest visual acuity. The conjunctiva is the mucus membrane which lines the eyelids and the eyeball, and ends abruptly at the limbus conjunctivae, the edge of the conjunctiva overlapping the cornea. The cornea is the clear, transparent anterior portion of the fibrous coat of the eye; it is important in light refraction and is covered with an epithelium that differs in many respects from the conjunctival epithelium.

The retina is the innermost, light sensitive portion of the eye, containing two types of photoreceptors, cones, which are responsible for color vision in brighter light, and rods, which are essential for vision in dim light but do not perceive colors. After light passes through the cornea, lens system, and the vitreous humor, it enters the retina from the inside; that is, it passes through the ganglion cells and nerve fibers, the inner and outer plexiform layers, the inner and outer nuclear layers, and the internal and external limiting membranes before it finally reaches the layer of photoreceptors located near the outside of the retina, just inside the outermost pigment epithelium layer. The cells of the pigment epithelium layer act as an anatomical barrier to liquids and substances located outside of the eye, forming the "blood-retina" barrier, and provide nourishment, oxygen, a source of functionally useful substances like vitamin A, and phagocytosis of decomposition products to photoreceptor cells. There is no anatomical connection between the pigment epithelium and the photoreceptor layer, permitting separation of the layers in some pathological situations.

When rods or cones are excited by light, signals are transmitted through successive neurons in the retina itself, into the optic nerve fibers, and ultimately to the cerebral cortex. Both rods and cones contain molecules that decompose on exposure to light and, in the process, excite the nerve fibers leading from the eye. The molecule in rods is rhodopsin. The three light-sensitive molecules in cones, collectively called iodopsin, have compositions only slightly different from that of rhodopsin and are maximally excited by red, blue, or green light, respectively.

Neither rods nor cones generate action potentials. Rather, the light-induced membrane hyperpolarization generated in the outer, photosensitive segment of a rod or cone cell is transmitted from the outer segment through the inner segment to the synaptic body by direct conduction of the electrical voltage itself, a process called electrotonic conduction. At the synaptic body, the membrane potential controls the release of an unknown transmitter molecule. In low light, rod and cone cell membranes are depolarized and the rate of transmitter release is greatest. Light-induced hyperpolarization causes a marked decrease in the release of transmitter molecules.

The transmitters released by rod and cone cells induce signals in the bipolar neurons and horizontal cells. The signals in both these cells are also transmitted by electrotonic conduction and not by action potential.

The rod bipolar neurons connect with as many as 50 rod cells, while the dwarf and diffuse bipolar cells connect with one or several cone cells. A depolarizing bipolar cell is stimulated when its connecting rods or cones are exposed to light. The release of transmitter molecules inhibits the depolarizing bipolar cell. Therefore, in the dark, when the rods and cones are secreting large quantities of transmitter molecules, the depolarizing bipolar cells are inhibited. In the light, the decrease in release of transmitter molecules from the rods and cones reduces the inhibition of the bipolar cell, allowing it to become excited. In this manner, both positive and negative signals can be transmitted through different bipolar cells from the rods and cones to the amacrine and ganglion cells.

As their name suggests, horizontal cells project horizontally in the retina, where they may synapse with rods, cones, other horizontal cells, or a combination of cells types. The function of horizontal cells is unclear, although some mechanism in the convergence of photoreceptor signaling has been postulated.

All types of bipolar cells connect with ganglion cells, which are of two primary types. A-type ganglion cells predominately connect with rod bipolar cells, while B-type ganglion cells predominately connect with dwarf and diffuse bipolar cells. It appears that A-type ganglion cells are sensitive to contrast, light intensity, and perception of movement, while B-type ganglion cells appear more concerned with color vision and visual acuity.

Like horizontal cells, the Amacrine cells horizontally synapse with several to many other cells, in this case bipolar cells, ganglion cells, and other Amacrine cells. The function of Amacrine cells is also unclear.

The axons of ganglion cells carry signals into the nerve fiber layer of the eye, where the axons converge into fibers which further converge at the optic disc, where they exit the eye as the optic nerve. The ganglion cells transmit their signals through the optic nerve fibers to the brain in the form of action potentials. These cells, even when unstimulated, transmit continuous nerve impulses at an average, baseline rate of about 5 per second. The visual signal is superimposed onto this baseline level of ganglion cell stimulation. It can be either an excitatory signal, with the number of impulses increasing above the baseline rate, or an inhibitory signal, with the number of nerve impulses decreasing below the baseline rate.

As part of the central nervous system, the eye is in some ways an extension of the brain; as such, it has a limited capacity for regeneration. This limited regeneration capacity further complicates the challenging task of improving vision, resolving dysfunction of the visual system, and/or treating or preventing ophthalmologic disorders. Many disorders of the eye, such as retinal photic injury, retinal ischemia-induced eye injury, age-related macular degeneration, free radical-induced eye diseases, as well as numerous other disorders, are considered to be entirely untreatable. Other ophthalmologic disorders, e.g., disorders causing permanent visual impairment, are corrected only by the use of ophthalmic devices and/or surgery, with varying degrees of success.

The immunosuppressant drugs FK506, rapamycin, and cyclosporin are well known as potent T-cell specific immunosuppressants, and are effective against autoimmunity, transplant or graft rejection, inflammation, allergic responses, other autoimmune or immune-mediated diseases, and infectious diseases. It has been disclosed that application of Cyclosporin, FK-506, Rapamycin, Buspirone, Spiperone, and/or their derivatives are effective in treating some ophthalmologic disorders of these types. Several ophthalmologic disorders or vision problems are known to be associated with autoimmune and immunologically-mediated activities; hence, immunomodulatory compounds are expected to demonstrate efficacy for treating those types of ophthalmologic disorders or vision problems.

The effects of FK506, Rapamycin, and related agents in the treatment of ophthalmologic diseases are disclosed in several U.S. patents (Goulet et al., U.S. Pat. No. 5,532,248; Mochizuki et al., U.S. Pat. No. 5,514,686; Luly et al., U.S. Pat. No. 5,457,111; Russo et al., U.S. Pat. No. 5,441,937; Kulkarni, U.S. Pat. No. 5,387,589; Asakura et al., U.S. Pat. No. 5,368,865; Goulet et al., U.S. Pat. No. 5,258,389; Armistead et al., U.S. Pat. No. 5,192,773; Goulet et al., U.S. Pat. No. 5,189,042; and Fehr, U.S. Pat. No. 5,011,844). These patents claim FK506 or Rapamycin related compounds and disclose the known use of FK506 or Rapamycin related compounds in the treatment of ophthalmologic disorders in association with the known immunosuppressive effects of FK506 and Rapamycin. The compounds disclosed in these patents are relatively large. Further, the cited patents relate to immunomodulatory compounds limited to treating autoimmunity or related diseases, or immunologically-mediated diseases, for which the efficacy of FK506 and Rapamycin is well known.

Other U.S. patents disclose the use of cyclosporin, Spiperone, Buspirone, their derivatives, and other immuno-suppressive compounds for use in the treatment of ophthalmologic diseases (Sharpe et al., U.S. Pat. No. 5,703,088; Sharpe et al., U.S. Pat. No. 5,693,645; Sullivan, U.S. Pat. No. 5,688,765; Sullivan, U.S. Pat. No. 5,620,921; Sharpe et al., U.S. Pat. No. 5,574,041; Eberle, U.S. Pat. No. 5,284,826; Sharpe et al., U.S. Pat. No. 5,244,902; Chiou et al., U.S. Pat. Nos. 5,198,454 and 5,194,434; and Kaswan, U.S. Pat. No. 4,839,342). These patents also relate to compounds useful for treating autoimmune diseases and cite the known use of cyclosporin, Spiperone, Buspirone, their derivatives, and other immunosuppressive compounds in treating ocular inflammation and other immunologically-mediated ophthalmologic diseases.

The immunosuppressive compounds disclosed in the prior art suppress the immune system, by definition, and also exhibit other toxic side effects. Accordingly, there is a need for non-immunosuppressant, small molecule compounds, and compositions and methods for use of such compounds, that are useful in improving vision; preventing, treating, and/or repairing visual impairment or dysfunction of the visual system; and preventing, treating, and/or resolving ophthalmologic disorders.

There are also a number of patents on non-immunosuppressive compounds disclosing methods of use for permitting or promoting wound healing (whether from injury or surgery); controlling intraocular pressure (often resulting from glaucoma); controlling neurodegenerative eye disorders, including damage or injury to retinal neurons, damage or injury to retinal ganglion cells, and macular degeneration; stimulating neurite outgrowth; preventing or reducing oxidative damage caused by free radicals; and treating impaired oxygen and nutrient supply, as well as impaired waste product removal, resulting from low blood flow. These non-immunosuppressive substances fall into one of two general categories: naturally occurring molecules, such as proteins, glycoproteins, peptides, hormones, and growth factors; and synthetic molecules.

Within the group of naturally occurring non-immunosuppressive molecules, several hormones, growth factors, and signaling molecules have been patented for use as supplements to naturally occurring quantities of such molecules, as well as for targeting of specific cells where the particular molecule does not naturally occur in a mature individual. These patents generally claim methods of use for reducing or preventing the symptoms of ocular disease, or arresting or reversing vision loss.

Specifically, Louis et al., U.S. Pat. Nos. 5,736,516 and 5,641,749, disclose the use of a glial cell line derived neurotrophic factor (GDNF) to stop or reverse the degeneration of retinal neurons (i.e. photoreceptors) and retinal ganglion cells caused by glaucoma, or other degenerative or traumatic retinal diseases or injuries. O'Brien, et al., U.S. Pat. Nos. 5,714,459 and 5,700,909, disclose the use of a glycoprotein, Saposin, and its derivatives for stimulating neurite outgrowth and increasing myelination. To stop or reverse degeneration of retinal neurons, LaVail et al., U.S. Pat. No. 5,667,968, discloses the use of a variety of neurotrophic proteins, including brain-derived neurotrophic factor, ciliary neurotrophic factor, neurotrophin-3 or neurotrophin-4, acidic or basic fibroblast growth factors, interleukin, tumor necrosis factor-$\alpha$, insulin-like growth factor-2 and other growth factors. Wong et al., U.S. Pat. No. 5,632,984, discloses the use of interferons, especially interferon $\alpha$-2a, for treating the symptoms of macular degeneration by reducing hemorrhage and limiting neovascularization. Finally, Wallace et al., U.S. Pat. No. 5,441,937, discloses the use of a lung-derived neurotrophic factor (NTF) to maintain the functionality of ciliary ganglion and parasympathetic neuron cells.

A key characteristic of factors derived from specific cell lines is their localization to specific cell lines or tissues; systemic treatment with these molecules would run a substantial risk of unintended, and potentially dangerous, effects in cell lines where the genes encoding these molecules are inactive. Similarly, hormones and growth factors often activate a large number of genes in many cell lines; again, non-localized application of these molecules would run a substantial risk of provoking an inappropriate, and potentially dangerous, response.

Within the category of synthetic molecules, most of the patented compounds are immunosuppressive and disclose uses in treating inflammatory, autoimmune, and allergic responses, as discussed above. A few others are non-immunosuppressive and claim the ability to treat cellular degeneration, and in some cases promote cellular regeneration, most often in the context of their antioxidant properties.

Specifically, Tso et al., U.S. Pat. No. 5,527,533, discloses the use of astaxanthin, a carotenoid antioxidant, for preventing or reducing photoreceptor damage resulting from the presence of free radicals. Similarly, Babcock et al., U.S. Pat. No. 5,252,319, discloses the use of antioxidant aminosteroids for treating eye disease and injury, by increasing resistance to oxidative damage. Freeman, U.S. Pat. No. 5,468,752, discloses the use of the antiviral phosphonyl-methoxyalkylcytosines to reduce abnormally increased intraocular pressure.

Naturally occurring hormones, growth factors, cytokines, and signaling molecules are generally multifunctional and activate many genes in diverse cell lines. The present compounds do not, thus avoiding the unexpected, and potentially dangerous, side effects of systemic use. Similarly, the present compounds also avoid the potential unexpected side effects of introducing cell line-specific molecules into other cell lines were they do not naturally occur.

The epithelial hair cells in the organ of Corti of the inner ear, transduce sound into neural activity, which is transmitted along the cochlear division of the eighth cranial nerve. This nerve consists of fibers from three types of neurons (Spoendllin, H. H., in Friedmann, I. Ballantyne, J., eds. "Ultrastructural Atlas of the Inner Ear", London, Butterworth, pp. 133–164, (1984)) 1) afferent neurons, which lie in the spiral ganglion and connect the cochlea to the brainstem; 2) efferent olivocochlear neurons, which originate in the superior olivary complex; and 3) autonomic adrenergic neurons, which originate in the cervical sympathetic trunk and innervate the cochlea. In the human, there are approximately 30,000 afferent cochlear neurons, with myelinated axons, each consisting of about 50 lamellae, and 4–6 $\mu$m in diameter. This histologic structure forms the basis of uniform conduction velocity, which is an important functional feature. Throughout the length of the auditory nerve, there is a trophic arrangement of afferent fibers, with 'basal' fibers wrapped over the centrally placed 'apical' fibers in a twisted rope-like fashion. Spoendlin (Spoendlin, H. H. in Naunton, R. F., Fernadex, C. eds., "Evoked Electrical Activity in the Auditory Nervous System", London, Academic Press, pp. 21–39, (1978)) identified two types of afferent neurons in the spiral ganglion on the basis of morphologic differences: type I cells (95%) are bipolar and have myelinated cell bodies and axons that project to the inner hair cells. Type II cells (5%) are monopolar with unmyelinated axons and project to the outer hair cells of the organ of Corti. Each inner hair cell is innervated by about 20 fibers, each of which synapses on only one cell. In contrast, each outer hair cell is innervated by approximately six fibers, and each fiber branches to supply approximately 10 cells. Within the cochlea, the fibers divide into: 1) an inner spiral group, which arises primarily ipsilaterally and synapses with the afferent neurons to the inner hair cells, and 2) a more numerous outer radial group, which arises mainly contralaterally and synapses directly with outer hair cells. There is a minimal threshold at one frequency, the characteristic or best frequency, but the threshold rises sharply for frequencies above and below this level (Pickles, J. O. in "Introduction to the Physiology of Hearing", London, Academic Press, pp. 71–106, (1982)). Single auditory nerve fibers therefore appear to behave as band-pass filters. The basilar membrane vibrates preferentially to different frequencies, at different distances along its length, and the frequency selectivity of each cochlear nerve fiber is similar to that of the inner hair cell to which the fiber is connected. Thus, each cochlear nerve fiber exhibits a tuning curve covering a different range of frequencies from its neighboring fiber (Evans, E. F. in Beagley H. A. ed., "Auditory investigation: The Scientific and Technological basis", New York, Oxford University Pressm (1979)). By this mechanism, complex sounds are broken down into component frequencies (frequency resolution) by the filters of the inner ear.

Impairment anywhere along the auditory pathway, from the external auditory canal to the central nervous system, may result in hearing loss. The auditory apparatus can be subdivided into the external and middle ear, inner ear and auditory nerve and central auditory pathways. Auditory information in humans is transduced from a mechanical signal to a neurally conducted electrical impulse by the action of approximately 15,000 epithelial cells (hair cells) and 30,000 first-order neurons (spiral ganglion cells) in the inner ear. All central fibers of spiral ganglion neurons form synapses in the cochlear nucleus of the pontine brainstem, The number of neurons involved in hearing increases dramatically from the cochlea to the auditory brain stem and the auditory cortex. All auditory information is transduced by only 15,000 hair cells, of which the so-called inner hair cells, numbering 3500, are critically important, since they from synapses with approximately 90 percent of the 30,000 primary auditory neurons. Thus, damage to a relatively few cells in the auditory periphery can lead to substantial hearing loss. Hence, most causes of sensorineural loss can be ascribed to lesions in the inner ear (Nadol, J. B., *New England Journal of Medicine*, (1993), 329:1092–1102).

Hearing loss can be on the level of conductivity, sensorineural and central level. Conductive hearing loss is caused by lesions involving the external or middle ear, resulting in the destruction of the normal pathway of airborne sound amplified by the tympanic membrane and the ossicles to the inner ear fluids. Sensorineural hearing loss is due to lesions of the central auditory pathways. These consist of the cochlear and dorsal olivary nucleus complex, inferior colliculi, medial geniculate bodies, auditory cortex in the temporal lobes and interconnecting afferent and efferent fiber tracts (Adams R. D. and Maurice, V., eds., in "Principles of Neurology", (1989), McGraw-Hill Information Services Company, pp. 226–246).

Trauma due to acoustic overstimulation is another leading cause of deafness. There is individual susceptibility to trauma from noise. Clinically important sensorineural hearing loss may occur in some people exposed to high-intensity noise, even below levels approved by the Occupational Safety and Health Agency (Osguthorpe, J. D., ed., Washington D.C., American Academy of Otolaryngology-Head and Neck Surgery Foundation, (1988)).

Demyelinating processes, such as multiple sclerosis, may cause sensorineural hearing loss (Noffsinger, D., et al., *Acto Otolaryngol. Suppl.* (Stockh.) (1972), 303:1–63). More recently, a form of immune-mediated sensorineural hearing loss has been recognized (McCabe, B. F., *Ann. Otol. Rhinol. Laryngol.* (1979), 88:585–9). The hearing loss is usually bilateral, is rapidly progressive (measured in weeks and months), and may or may not be associated with vestibular symptoms.

A variety of tumors, both primary and metastatic, can produce either a conductive hearing loss, or a sensorineural hearing loss, by invading the inner ear or auditory nerve (Houck, J. R., et al., *Otolaryngol. Head Neck Surg.* (1992), 106:92–7). A variety of degenerative disorders of unknown cause can produce sensorineural hearing loss. Meniere's syndrome (Nadol, J. B., ed., "Meniere's Disease: Pathogenesis, Pathophysiology, Diagnosis, And Treatment," Amsterdam: Kugler & Ghedini (1989)), characterized by fluctuating sensorineural hearing loss, episodic certigo, and tinnitus, appears to be caused by a disorder of fluid homeostasis within the inner ear, although the pathogenesis remains unknown. Sudden idiopathic sensorineural hearing loss (Wilson, W. R., et al., *Arch. Otolaryngol.* (1980), 106:772–6), causing moderate-to-severe sensorineural deafness, may be due to various causes, including inner ear ischemia and viral labyrinthitis.

Regardless of the cause, there exists a need to prevent or treat sensorineural hearing loss. The present invention provides such a method.

BRIEF SUMMARY OF THE INVENTION

The present invention is directed to novel hydantoin derivative compounds, and their preparation and use for treating neurodegenerative disorders, for treating alopecia and related hair loss disorders, for treating vision disorders and/or improving vision, for treating memory impairment and/or enhancing memory performance, and for treating sensorineural hearing loss.

These compounds stimulate neuronal regeneration and outgrowth and as such are useful for treating neurological disorders and neurodegenerative diseases. These compounds also promote hair growth and as such are useful for treating hair loss disorders. These compounds also are useful for treating vision disorders, improving vision, treating memory impairment, enhancing memory performance, or treating hearing loss. A preferred feature of the compounds of the present invention is that they do not exert any significant immunosuppressive activity and/or are non-immunosuppressive.

A preferred embodiment of this invention is a compound having the formula I:

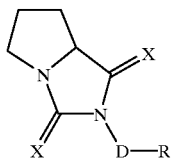

I where
each X independently is O, S, or $NR_2$;
$R_2$ is selected from the group consisting of cyano, nitro, hydrogen, $C_1$–$C_4$ alkyl, hydroxy, and $C_1$–$C_4$ alkoxy;
D is a direct bond or a $C_1$–$C_8$ alkyl or alkenyl;
R is selected from the group consisting of hydrogen, phenyl, biphenyl, cyclopropyl, cyclobutyl, cyclopentyl, cycloheptyl, cyclooctyl, naphthyl, 1,2,3,4-tetrahydronaphthyl, indenyl, azulenyl, fluorenyl, anthracenyl, isoindolyl, indolinyl, benzofuranyl, benzothiophenyl, indazolyl, benzimidazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, benzofuranyl, thiophenyl, imidazolyl, oxazolyl, benzoxazolyl, benzoxazinyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, benzopyranyl, thienyl, tetrahydroisoquinolinyl, cinnolinyl, phthalazinyl, quinazolinyl, quinoxalinyl, naphthyridinyl, pteridinyl, carbazolyl, phenazinyl, phenothiazinyl, phenoxazinyl, and adamantyl;
wherein R may be optionally substituted with one substituent which is selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenyl, phenoxy, benzyloxy, and amino;
or a pharmaceutically acceptable salt, ester, or solvate thereof;
wherein when R is hydrogen, D is a $C_5$–$C_7$ alkyl or $C_5$–$C_8$ alkenyl;
wherein when R is phenyl, R must be substituted with phenyl, hydroxyl, trifluoromethyl, $C_2$–$C_6$ straight or branched chain alkyl or alkenyl, $C_3$–$C_4$ alkoxy or $C_2$–$C_4$ alkenyloxy, phenoxy, or benzyloxy;
wherein when R is 4-trifluoromethylphenyl, both X substituents must be O.

Another preferred embodiment of this invention is a compound of formula II:

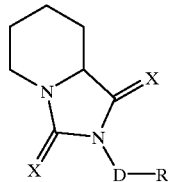

II where
each X independently is O, S, or $NR_2$;
$R_2$ is selected from the group consisting of cyano, nitro, hydrogen, $C_1$–$C_4$ alkyl, hydroxy, and $C_1$–$C_4$ alkoxy;
D is a direct bond or a $C_1$–$C_8$ alkyl or alkenyl;
R is selected from the group consisting of hydrogen, phenyl, biphenyl, cyclopropyl, cyclobutyl, cyclopentyl, cyclohexyl, cycloheptyl, cyclooctyl, 1,2,3,4-tetrahydronaphthyl, indenyl, azulenyl, fluorenyl, anthracenyl, indolyl, isoindolyl, indolinyl, benzofuranyl, benzothiophenyl, indazolyl, benzimidazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzopyranyl, thiazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, naphthyridinyl, pteridinyl, carbazolyl, acridinyl, phenazinyl, phenothiazinyl, phenoxazinyl, and adamantyl;
wherein R may be optionally substituted with one substituent which is selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenyl, phenoxy, benzyloxy, and amino;
or a pharmaceutically acceptable salt, ester, or solvate thereof;
wherein when R is hydrogen, D is a $C_5$–$C_8$ alkyl or alkenyl;
wherein when R is phenyl, R must be substituted with $C_2$–$C_3$ or $C_5$–$C_6$ straight or branched chain alkyl or alkenyl, $C_3$–$C_4$ alkoxy or $C_2$–$C_4$ alkenyloxy, phenyl, phenoxy, benzyloxy, or amino.

Another preferred embodiment of this invention is a pharmaceutical composition containing:
(i) an effective amount of a hydantoin derivative compound of formula III:

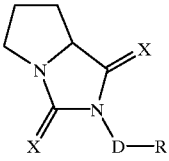

III where
each X independently is O, S, or $NR_2$;
$R_2$ is selected from the group consisting of cyano, nitro, hydrogen, $C_1$–$C_4$ alkyl, hydroxy, and $C_1$–$C_4$ alkoxy;

D is a direct bond or $C_1$–$C_8$ alkyl or alkenyl;

R is hydrogen, or an alicyclic or aromatic, mono-, bi- or tricyclic, carbo- or heterocyclic ring;

wherein R is optionally substituted with one substituent selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenyl, phenoxy, benzyloxy, and amino; and (ii) a pharmaceutically acceptable carrier.

Another preferred embodiment of this invention is a pharmaceutical composition containing:

(i) an effective amount of a hydantoin derivative compound of formula IV:

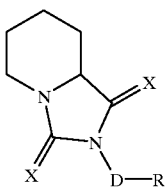

IV where each X independently is O, S, or $NR_2$;

$R_2$ is selected from the group consisting of cyano, nitro, hydrogen, $C_1$–$C_4$ alkyl, hydroxy, and $C_1$–$C_4$ alkoxy;

D is a direct bond or $C_1$–$C_8$ alkyl or alkenyl;

R is hydrogen, or an alicyclic or aromatic, mono-, bi- or tricyclic, carbo- or heterocyclic ring;

wherein R is optionally substituted with one substituent selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenyl, phenoxy, benzyloxy, and amino; and (ii) a pharmaceutically acceptable carrier.

For neurotrophic compositions, a neurotrophic factor different from the present inventive compounds may also be administered or otherwise included in the composition.

Another preferred embodiment of the invention is a method of treating a neurological disorder in an animal, comprising administering to the animal an effective amount of the compound of formulae III or IV to stimulate growth of damaged peripheral nerves or to promote neuronal regeneration.

Another preferred embodiment of the invention is a method of stimulating growth of damaged peripheral nerves, comprising administering to a damaged peripheral nerve an effective amount of the compound of formulae III or IV to stimulate or promote growth of the damaged peripheral nerve.

Another preferred embodiment of the invention is a method of promoting neuronal regeneration and growth in animals, comprising administering to an animal an effective amount of the compound of formulae III or IV to promote neuronal regeneration.

Another preferred embodiment of the invention is a method of preventing neurodegeneration in animals, comprising administering to an animal an effective amount of the compound of formulae III or IV to prevent neurodegeneration.

Another preferred embodiment of the invention is a method for treating alopecia or promoting hair growth in an animal, comprising administering to an animal an effective amount of the compound of formulae III or IV.

Another preferred embodiment of this invention is a method for treating a vision disorder, improving vision, treating memory impairment, enhancing memory performance, or treating sensorineural hearing loss in an animal, comprising administering to an animal an effective amount of the compound of formula III or IV.

The present invention further contemplates a process for preparing the hydantoin derivative compounds of the invention, comprising acidifying an intermediate compound.

The present invention further contemplates the compound(s) of the invention for use in treatment of a disease. In particular, the present invention contemplates the compound(s) of the invention for use in treatment of the disorders enumerated herein.

The invention further contemplates the compound(s) of the invention for use in the preparation of a medicament or pharmaceutical composition. In particular, the invention contemplates the compound(s) of the invention for use in the preparation of a medicament or pharmaceutical composition for treatment of the disorders enumerated herein.

The invention also provides for the use of compound(s) of the invention for treating a disease. In particular, the invention provides for the use of compound(s) of the invention for treating the disorders enumerated herein.

The invention also provides for the use of compound(s) of the invention in the manufacture of a medicament or pharmaceutical composition. In particular, the invention provides for the use of compound(s) of the invention in the manufacture of a medicament or pharmaceutical composition for the treatment of the disorders enumerated herein. Such pharmaceutical compositions include, as appropriate to the specific disorder, topical, systemic, oral or injectable formulations. It is further contemplated that the compound(s) of the invention may be administered with an effective amount of a second therapeutic agent for the treatment of the enumerated disorders. A variety of pharmaceutical formulations and different delivery techniques are described in further detail below.

DETAILED DESCRIPTION OF THE INVENTION

Definitions

"Alkenyl" means a branched or unbranched unsaturated hydrocarbon chain comprising a designated number of carbon atoms. For example, $C_2$–$C_6$ straight or branched alkenyl hydrocarbon chain contains 2 to 6 carbon atoms having at least one double bond, and includes but is not limited to substituents such as ethenyl, propenyl, iso-propenyl, butenyl, iso-butenyl, tert-butenyl, n-pentenyl, n-hexenyl, and the like. It is also contemplated as within the scope of the present invention that "alkenyl" may also refer to an unsaturated hydrocarbon chain wherein any of the carbon atoms of said alkenyl are optionally replaced with O, NH, S, or $SO_2$. For example, carbon 2 of 4-pentene can be replaced with O to form (2-propene)oxymethyl.

"Alkoxy" means the group —OR wherein R is alkyl as herein defined. Preferably, R is a branched or unbranched saturated hydrocarbon chain containing 1 to 6 carbon atoms.

"Alkyl" means a branched or unbranched saturated hydrocarbon chain comprising a designated number of carbon atoms. For example, $C_1$–$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentyl, n-hexyl, and the like. It is also contemplated as within the scope of the present invention that "alkyl" may also refer to a hydrocarbon chain wherein any of the carbon atoms of said alkyl are optionally replaced with O, NH, S, or $SO_2$. For example, carbon 2 of n-pentyl can be replaced with O to form propyloxymethyl.

"Alopecia" refers to deficient hair growth and partial or complete loss of hair, including without limitation androgenic alopecia (male pattern baldness), toxic alopecia, alopecia senilis, alopecia areata, alopecia pelada and trichotillomania. Alopecia results when the pilar cycle is disturbed. The most frequent phenomenon is a shortening of the hair growth or anagen phase due to cessation of cell proliferation. This results in an early onset of the catagen phase, and consequently a large number of hairs in the telogen phase during which the follicles are detached from the dermal papillae, and the hairs fall out. Alopecia has a number of etiologies, including genetic factors, aging, local and systemic diseases, febrile conditions, mental stresses, hormonal problems, and secondary effects of drugs.

"Aralkyl" refers to alkyl or alkylene (alkenyl) chain which is substituted with aryl, heteroaryl, carbocycle or heterocycle, or alternatively one or more aryl, heteroaryl, carbocycle, or heterocycle(s) which is/are substituted with alkyl or alkenyl, i.e. 'Alkyl/alkylene which is substituted with Ar' or 'Ar which is substituted with alkyl/alkylene'.

"Aryl" or "aromatic" refers to an aromatic carbocyclic or heterocyclic group having a single ring, for example a phenyl ring; multiple rings, for example biphenyl; or multiple condensed rings in which at least one ring is aromatic, for example naphthyl, 1,2,3,4-tetrahydronaphthyl, anthryl, or phenanthryl, which can be unsubstituted or substituted with one or more other substituents as defined above. The substituents attached to a phenyl ring portion of an aryl moiety in the compounds of the invention may be configured in the ortho-, meta-, or para-orientations orientations.

Examples of typical aryl moieties included in the scope of the present invention may include, but are not limited to, the following:

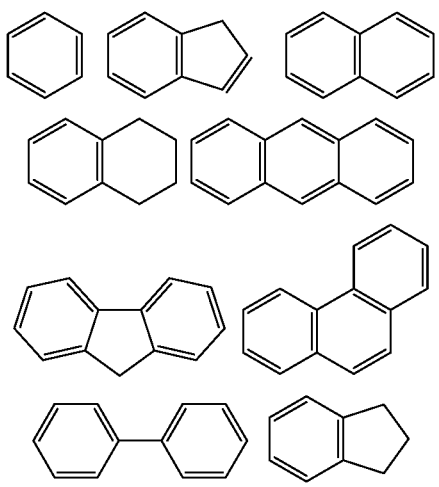

"Carbocycle" or "carbocyclic" refers to an organic cyclic moiety in which the cyclic skeleton is comprised of only carbon atoms, whereas the term "heterocycle" or "heterocyclic" refers to an organic cyclic moiety in which the cyclic skeleton contains one or more heteroatoms selected from nitrogen, oxygen, or sulfur, and which may or may not include carbon atoms. Thus, the term "carbocycle" refers to a carbocyclic moiety containing the indicated number of carbon atoms. The term "$C_3$–$C_8$ cycloalkyl", therefore, refers to an organic cyclic substituent in which three to eight carbon atoms form a three, four, five, six, seven, or eight-membered ring, including, for example, a cyclopropyl, cyclobutyl, cyclopentyl, cyclohexyl, cycloheptyl, or cyclooctyl ring.

As used herein, "carbocyclic" or "heterocyclic" may also refer to two or more cyclic ring systems, which are fused to form, for example, bicyclic, tricyclic, or other similar bridged ring substituents (e.g. adamantyl) or multiple condensed ring systems.

"Enhancing memory performance" refers to improving or increasing the mental faculty by which to register, retain or recall past experiences, knowledge, ideas, sensations, thoughts or impressions.

"Eye" refers to the anatomical structure responsible for vision in humans and other animals, and encompasses the following anatomical structures, without limitation: lens, vitreous body, ciliary body, posterior chamber, anterior chamber, pupil, cornea, iris, canal of Schlemm, zonules of Zinn, limbus, conjunctiva, choroid, retina, central vessels of the retina, optic nerve, fovea centralis, macula lutea, and sclera.

"Halo" means at least one fluoro, chloro, bromo, or iodo moiety.

"Heterocycle" or "heterocyclic", as used herein, refers to a saturated, unsaturated or aromatic carbocyclic group having a single ring, multiple fused rings(for example, bicyclic, tricyclic, or other similar bridged ring systems or substituents), or multiple condensed rings, and having at least one hetero atom such as nitrogen, oxygen or sulfur within at least one of the rings. This term also includes "Heteroaryl" which refers to a heterocycle in which at least one ring is aromatic. Any heterocyclic or heteroaryl group can be unsubstituted or optionally substituted with one or more groups, as defined above. Further, bi- or tricyclic heteroaryl moieties may comprise at least one ring which is either completely or partially saturated.

In the context of the invention, useful carbo- and heterocyclic rings include, for example and without limitation, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, and adamantyl.

As one skilled in the art will appreciate, such heterocyclic moieties may exist in several isomeric forms, all of which are encompassed by the present invention. For example, a 1,3,5-triazine moiety is isomeric to a 1,2,4-triazine group. Such positional isomers are to be considered within the scope of the present invention. Likewise, the heterocyclic or heteroaryl groups can be bonded to other moieties in the compounds of the present invention. The point(s) of attachment to these other moieties is not to be construed as limiting on the scope of the invention. Thus, by way of example, a pyridyl moiety may be bound to other groups through the 2-, 3-, or 4-position of the pyridyl group. All such configurations are to be construed as within the scope of the present invention.

Examples of heterocyclic or heteroaryl moieties included in the scope of the present invention may include, but are not limited to, the following:

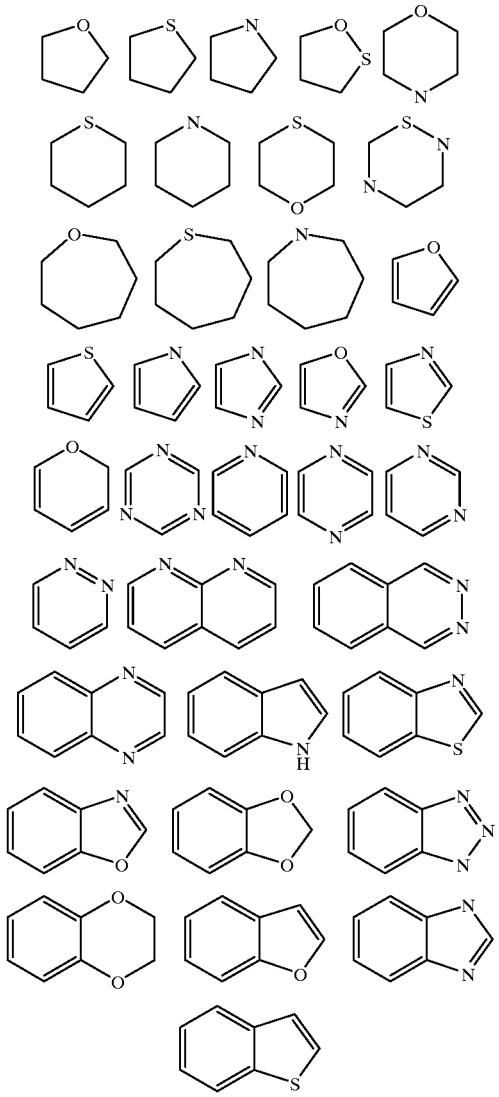

The *Condensed Chemical Dictionary* (Tenth Edition) revised by Gessner G. Hawley (1981) defines "hydantoins" as compounds having the chemical formula NHCONH-COCH$_2$. The "hydantoin derivatives" contemplated by the present invention have the general structure:

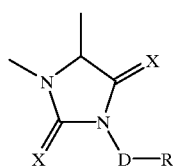

wherein the five membered ring depicted is part of a bicyclic ring structure and wherein each X independently can be O, S, or NR$_2$. In particular, one class of hydantoin derivative compounds contemplated by the present invention has the structure:

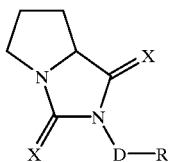

Another class of hydantoin derivative compounds contemplated by the present invention has the structure:

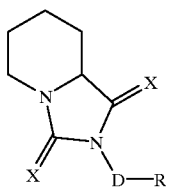

"Isomers" are different compounds that have the same molecular formula and includes cyclic isomers such as (iso)indole and other isomeric forms of cyclic moieties. "Stereoisomers" are isomers that differ only in the way the atoms are arranged in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

"Memory impairment" refers to a diminished mental registration, retention or recall of past experiences, knowledge, ideas, sensations, thoughts or impressions. Memory impairment may affect short and long-term information retention, facility with spatial relationships, memory (rehearsal) strategies, and verbal retrieval and production. Common causes of memory impairment are age, severe head trauma, brain anoxia or ischemia, alcoholic-nutritional diseases, and drug intoxications. Examples of memory impairment include, without limitation, benign forgetfulness, amnesia and any disorder in which memory deficiency is present, such as Korsakoff's amnesic psychosis, dementia and learning disorders.

The term "middle-ear" refers to the space between the tympanic membrane and the inner ear. This location is external to all inner ear tissue and an invasive procedure might not be required to access this region if a formulation capable of penetrating through the tympanic membrane is administered. Otherwise, the material will be introduced to the middle ear by injection through the tympanic membrane or, in case repeated administrations are needed, a hole can be made in the tympanic membrane. An opening in the tympanic membrane is a frequent procedure, performed on an office-visit basis, in cases such as infections of the middle ear (usually in children). The opening generally closes spontaneously after a few days.

"Neopsic factors" or "neopsics" refers to compounds useful in treating vision loss, preventing vision degeneration, or promoting vision regeneration.

"Neopsis" refers to the process of treating vision loss, preventing vision degeneration, or promoting vision regeneration.

"Neurotrophic" as used herein includes without limitation the ability to stimulate neuronal regeneration or growth, and/or the ability to prevent or treat neurodegeneration.

"Non-immunosuppressive" as used herein refers to the inability of the compounds of the present invention to trigger an immune response when compared to a control such as FK506 or cyclosporin A. Assays for determining immunosuppression are well known to those of ordinary skill in the art. Specific, non-limiting examples of well known assays include PMA and OKT3 wherein mitogens are used to stimulate proliferation of human peripheral blood lymphocytes (PBC) and the compounds are evaluated on their ability to inhibit such proliferation.

"Ophthalmological" refers to anything about or concerning the eye, without limitation, and is used interchangeably with "ocular," "ophthalmic," "ophthalmologic," and other such terms, without limitation.

"Pharmaceutically acceptable carrier" as used herein refers to any carrier, diluent, excipient, suspending agent, lubricating agent, adjuvant, vehicle, delivery system, emulsifier, disintegrant, absorbent, preservative, surfactant, colorant, flavorant, or sweetener. For these purposes, the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

"Pharmaceutically acceptable salt", as used herein, refers to an organic or inorganic salt which is useful in the treatment of a warm-blooded animal in need thereof. Such salts can be acid or basic addition salts, depending on the nature of the inventive compound to be used.

Further, the compounds of the invention may exist as crystalline solids which can be crystallized from common solvents such as ethanol, N,N-dimethyl-formamide, water, or the like. Thus, crystalline forms of the compounds of the invention may exist as solvates and/or hydrates of the parent compounds or their pharmaceutically acceptable salts. All of such forms likewise are to be construed as falling within the scope of the invention.

"Pilar cycle" refers to the life cycle of hair follicles, and includes three phases:

(1) the anagen phase, the period of active hair growth which, insofar as scalp hair is concerned, lasts about three to five years;
(2) the catagen phase, the period when growth stops and the follicle atrophies which, insofar as scalp hair is concerned, lasts about one to two weeks; and
(3) the telogen phase, the rest period when hair progressively separates and finally falls out which, insofar as scalp hair is concerned, lasts about three to four months.

Normally 80 to 90 percent of the follicles are in the anagen phase, less than 1 percent being in the catagen phase, and the rest being in the telogen phase. In the telogen phase, hair is uniform in diameter with a slightly bulbous, non-pigmented root. By contrast, in the anagen phase, hair has a large colored bulb at its root.

"Preventing neurodegeneration" as used herein includes the ability to inhibit or prevent neurodegeneration in patients newly diagnosed as having a neurodegenearative disease, or at risk of developing a new degenerative disease and for inhibiting or preventing further neurodegeneration in patients who are already suffering from or have symptoms of a neurodegenerative disease when the compounds are given concurrently.

"Preventing vision degeneration" as used herein includes the ability to prevent degeneration of vision in patients newly diagnosed as having a degenerative disease affecting vision, or at risk of developing a new degenerative disease affecting vision, and for preventing further degeneration of vision in patients who are already suffering from or have symptoms of a degenerative disease affecting vision.

"Primary ring structure" refers to a 5- or 6-membered ring structure which is depicted in the formula drawings herein. Such definition shall apply to only one ring structure in any molecule described in this application, regardless of the number or confirmation of any substituent cyclic structures.

"Promoting hair growth" refers to maintaining, inducing, stimulating, accelerating, or revitalizing the germination of hair.

"Promoting vision regeneration" refers to maintaining, improving, stimulating or accelerating recovery of, or revitalizing one or more components of the visual system in a manner which improves or enhances vision, either in the presence or absence of any ophthalmologic disorder, disease, or injury.

The term "small molecule" refers to the molecular weight of the compounds of the invention as compared to FK506. Thus, the term "small molecule" includes molecular weights less than about 800 Daltons (m.w.), and novel subranges or limits below the same including about 100 to about 750 m.w., about 150 to about 500 m.w., about 150 to about 350 m.w., about 200 to about 300 m.w., about 210 to about 280 m.w., about 220 to about 260, and about 240 m.w. The term "spatially small molecule" refers to the capability of the compounds to fit entirely or substantially within the binding cavity of FKBP-12 as compared to FK506.

"Treating" or "treatment" as used herein covers any treatment of a disease and/or condition in an animal, particularly a human, and includes:

(i) preventing a disease and/or condition from occurring in a subject which may be predisposed to the disease and/or condition but has not yet been diagnosed as having it;
(ii) inhibiting the disease and/or condition, i.e., arresting its development; or
(iii) relieving the disease and/or condition, i.e., causing regression of the disease and/or condition.

"Treating alopecia" refers to:
(i) preventing alopecia in an animal which may be predisposed to alopecia; and/or
(ii) inhibiting, retarding or reducing alopecia; and/or
(iii) promoting hair growth; and/or
(iv) prolonging the anagen phase of the hair cycle; and/or
(v) converting vellus hair to growth as terminal hair.

Terminal hair is coarse, pigmented, long hair in which the bulb of the hair follicle is seated deep in the dermis. Vellus hair, on the other hand, is fine, thin, non-pigmented short hair in which the hair bulb is located superficially in the dermis. As alopecia progresses, the hairs change from the terminal to the vellus type.

"Vision", as used herein, refers to the ability of humans and other animals to process images, and is used interchangeably with "sight", "seeing", and other such terms, without limitation.

"Vision disorder" refers to any disorder that affects or involves vision, including without limitation visual impairment, orbital disorders, disorders of the lacrimal apparatus, disorders of the eyelids, disorders of the conjunctiva, disorders of the cornea, cataracts, disorders of the uveal tract, disorders of the optic nerve or visual pathways, free radical induced eye disorders and diseases, immunologically-mediated eye disorders and diseases, eye injuries, and symptoms and complications of eye disease, eye disorder, or eye injury.

"Visual impairment" refers to any dysfunction in vision including without limitation disturbances or diminution in vision (e.g., binocular, central, peripheral, scotopic), visual acuity for objects near and for, visual field, ocular motility, color perception, adaptation to light and dark, accommodation, refraction, and lacrimation. See *Physicians' Desk Reference (PDR) for Ophthalmology*, 16th Edition, 6:47 (1988).

"Warm-blooded animal" includes a mammal, including a member of the human, equine, porcine, bovine, murine, canine or feline species. In the case of a human, the term "warm-blooded animal" may also be referred to as a "patient". Further, as used herein, "a warm blooded animal in need thereof" refers to a warm-blooded animal which is susceptible to a disorder due to genetic or environmental conditions or predispositions. This term also refers to a warm blooded animal which has already suffered some degree of injury or damage because of genetic or environmental conditions to which the animal has been exposed or to which it has been predisposed. Environmental conditions can include treatment with a therapeutic compound, as well as other types of injury or insult.

Further, as used throughout the teaching of the invention, a designation of:

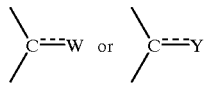

wherein W or Y is $H_2$, or similar designations, is meant to denote that two hydrogen atoms are attached to the noted carbon and that the bonds to each hydrogen are single bonds.

Compounds of the Invention

The present invention relates to the surprising discovery that the inventive hydantoin and hydantoin derivative compounds are neurotrophic, are able to treat alopecia, are able to treat vision and memory disorders, and are able to treat sensorineural hearing loss. Accordingly, a novel class of hydantoin derivative compounds is provided. A preferred feature of the compounds of the present invention is that they do not exert any significant immunosuppressive activity.

The neurotrophic compounds of this invention can be periodically administered to a patient undergoing treatment for neurological disorders or for other reasons in which it is desirable to stimulate neuronal regeneration and growth, such as in various peripheral neuropathic and neurological disorders relating to neurodegeneration. The compounds of this invention can also be administered to mammals other than humans for treatment of various mammalian neurological disorders.

The novel compounds of the present invention possess an excellent degree of neurotrophic activity. This activity is useful in the stimulation of damaged neurons, the promotion of neuronal regeneration, the prevention of neurodegeneration, and in the treatment of several neurological disorders known to be associated with neuronal degeneration and peripheral neuropathies. The neurological disorders that may be treated include but are not limited to: trigeminal neuralgia, glossopharyngeal neuralgia, Bell's Palsy, myasthenia gravis, muscular dystrophy, amyotrophic lateral sclerosis, progressive muscular atrophy, progressive bulbar inherited muscular atrophy, herniated, ruptured or prolapsed invertebrate disk syndromes, cervical spondylosis, plexus disorders, thoracic outlet destruction syndromes, peripheral neuropathic such as those caused by lead, dapsone, ticks, prophyria, or Gullain-Barré syndrome, multiple sclerosis, stroke and ischemia associated with stroke, neural paropathy, other neurodegenerative diseases, motor neuron diseases, sciatic crush, peripheral neuropathy, particularly neuropathy associated with diabetes, spinal cord injuries and facial nerve crush, Huntington's Disease, Alzheimer's disease, and Parkinson's disease.

The above discussion relating to the utility and administration of the compounds of the present invention also applies to the pharmaceutical compositions of the present invention.

For these purposes, the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

For oral administration, the compounds of the present invention may be provided in any suitable dosage form known in the art. For example, the compositions may be incorporated into tablets, powders, granules, beads, chewable lozenges, capsules, liquids, aqueous suspensions or solutions, or similar dosage forms, using conventional equipment and techniques known in the art. Tablet dosage forms are preferred. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient.

When preparing dosage form incorporating the compositions of the invention, the compounds may also be blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethylcellulose and sodium starch glycolate; suspending agents, such as povidone, polyvinyl alcohol, and the like; absorbents, such as silicon dioxide; preservatives, such as methylparaben, propylparaben, and sodium benzoate; surfactants, such as sodium lauryl sulfate, polysorbate 80, and the like; colorants such as F.D.& C. dyes and lakes; flavorants; and sweeteners.

Compositions and methods of the invention also may utilize controlled release technology. Thus, for example, the inventive compounds may be incorporated into a hydrophobic polymer matrix for controlled release over a period of days. Such controlled release films are well known to the art. Particularly preferred are transdermal delivery systems. Other examples of polymers commonly employed for this purpose that may be used in the present invention include nondegradable ethylene-vinyl acetate copolymer and degradable lactic acid-glycolic acid copolymers which may be used externally or internally. Certain hydrogels such as poly(hydroxyethylmethacrylate) or poly(vinylalcohol) also may be useful, but for shorter release cycles then the other polymer releases systems, such as those mentioned above.

To be effective therapeutically as central nervous system targets, the compounds of the present invention should readily penetrate the blood-brain barrier when peripherally administered. Compounds which cannot penetrate the blood-brain barrier can be effectively administered by an intraventricular route or other appropriate delivery system suitable for administration to the brain.

The compounds of the present invention may be administered in the form of sterile injectable preparations, for example, as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil may be employed including synthetic mono- or di-glycerides. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

The compounds of this invention may also be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax and polyethylene glycols.

The compounds of this invention may also be administered topically, especially when the conditions addressed for treatment involve areas or organs readily accessible by topical application, including neurological disorders of the eye, the skin, or the lower intestinal tract. Suitable topical formulations are readily prepared for each of these areas.

For topical application to the eye, or ophthalmic use, the compounds can be formulated as micronized suspensions in isotonic, pH adjusted sterile saline, or, preferably, as solutions in isotonic, pH adjusted sterile saline, either with or without a preservative such as benzylalkonium chloride. Alternatively for the ophthalmic uses the compounds may be formulated in an ointment such as petrolatum.

For topical application to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract an be effected in a rectal suppository formulation (see below) or in a suitable enema formulation.

Dosage levels on the order of about 0.1 mg to about 10,000 mg of the active ingredient compound are useful in the treatment of the above conditions, with preferred levels of about 0.1 mg to about 1,000 mg. It is understood, however, that a specific dose level for any particular patient will vary depending upon a variety of factors, including the activity of the specific compound employed; the age, body weight, general health, sex and diet of the patient; the time of administration; the rate of excretion; drug combination; the severity of the particular disease or disorder being treated; and the form of administration. Typically, in vitro dosage-effect results provide useful guidance on the proper doses for patient administration. Studies in animal models are also helpful. The considerations for determining the proper dose levels are well known in the art.

The specific dose may be calculated according to considerations of body weight, body surface area or organ size. Further refinement of the calculations necessary to determine the appropriate dosage for treatment involving each of the above mentioned formulations is routinely made by those of ordinary skill in the art and is within the ambit of tasks routinely performed, especially in light of the dosage information and assays disclosed herein. Appropriate dosages may be determined using established assays in conjunction with appropriate dose-response data. One skilled in the art will appreciate that the dosage used in localized formulations of the invention normally will be smaller as compared to that used in a systemic injection or oral administration.

To effectively treat alopecia or promote hair growth, the compounds used in the inventive methods and pharmaceutical compositions must readily affect the targeted areas. For these purposes, the compounds are preferably administered topically to the skin.

The compounds can be administered with other hair revitalizing agents. Specific dose levels for the other hair revitalizing agents will depend upon the factors previously stated and the effectiveness of the drug combination. Other routes of administration known in the pharmaceutical art are also contemplated by this invention.

Specific embodiments of the inventive compounds are presented in Tables I and II. The present invention contemplates employing the compounds of Tables I and II, below, for use in compositions and methods to prevent and/or treat a neurological disorder in an animal, for use in compositions and methods to treat alopecia and promote hair growth in an animal, for use in compositions and methods to treat a vision disorder, improve vision, treat memory impairment, and enhance memory performance, and for use in compositions and methods to treat a sensorineural hearing loss in an animal, and all the other uses suggested in this specification.

TABLE I

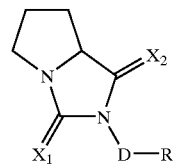

(I)

| No. | $X_1$ | $X_2$ | D | R |
|---|---|---|---|---|
| 1 | O | O | bond | Naphthyl |
| 2 | O | O | bond | 2-(Phenyl)phenyl |
| 3 | O | O | bond | 4-Trifluoromethylphenyl |
| 4 | S | O | methyl | Phenyl |
| 5 | O | O | hexyl | Hydrogen |
| 6 | O | O | bond | 2-(Ethyl)phenyl |
| 7 | S | O | propyl | Phenyl |
| 8 | S | O | ethyl | Phenyl |
| 9 | O | O | heptyl | Hydrogen |

TABLE I-continued (I)

| No. | $X_1$ | $X_2$ | D | R |
|---|---|---|---|---|
| 10 | O | O | octyl | Hydrogen |
| 11 | S | O | pentyl | 3-Pyridyl |
| 12 | O | O | propyl | Phenyl |
| 13 | O | O | bond | 3-(Hydroxy)phenyl |
| 14 | O | O | bond | 4-(tert-butyl)phenyl |
| 15 | O | O | bond | 2-(Prop-2-enyl)phenyl |
| 16 | O | O | bond | 3-(Ethoxy)phenyl |
| 17 | S | O | bond | Cyclopentyl |
| 18 | S | O | bond | Quinolinyl |
| 19 | O | O | hexyl | Phenyl |
| 20 | O | O | ethyl | Phenyl |
| 21 | O | O | bond | Cyclopentyl |
| 22 | S | S | bond | 2-thienyl |
| 23 | O | S | bond | 2-thienyl |
| 24 | O | O | bond | 2-oxazolyl |
| 25 | S | O | bond | 2-furyl |
| 26 | O | NH | bond | 3-furyl |
| 27 | O | NH | hexyl | 4-furyl |
| 28 | O | S | bond | Adamantyl |
| 29 | S | N—CN | bond | Carbazole |
| 30 | O | N—$NO_2$ | bond | Isoquinoline |
| 31 | NH | NH | methyl | 3-Pyridinyl |
| 32 | O | $NCH_3$ | hexyl | Hydrogen |
| 33 | NOH | O | bond | 2-Thiazolyl |
| 34 | $NOCH_3$ | S | bond | 4-(tert-butyl)phenyl |
| 35 | O | S | bond | Cyclohexyl |
| 36 | O | O | bond | Phenyl |
| 37 | S | O | bond | Phenyl |

Preferred compounds of TABLE I are named as follows:

(7aS)-2-(1-Naphthyl)perhydropyrrolo[1,2-c]imidazole-1,3-dione (Compound 1), (7aS)-2-(2'-Phenyl)phenylperhydropyrrolo[1,2-c]imidazole-1,3-dione (Compound 2), (7aS)-2-(4-(Trifluoromethyl)phenyl)perhydropyrrolo[1,2-c]imidazole-1,3-dione (Compound 3), 2-benzyl-3-thioxo-2,5,6,7,7a-pentahydro-2-azapyrrolizin-1-one (Compound 4), 2-hexyl-2,5,6,7,7a-pentahydro-2-azapyrrolizine-1,3-dione (Compound 5), 2-(2-ethyl)phenyl-2,5,6,7,7a-pentahydro-2-azapyrrolizin-1,3-dione (Compound 6), 2-(3-phenylpropyl)-3-thioxo-2,5,6,7,7a-pentahydro-2-azapyrrolizin-1-one (Compound 7), 2-(2-phenylethyl)-3-thioxo-2,5,6,7,7a-pentahydro-2-azapyrrolizin-1-one (Compound 8), (7aS)-2-Cyclohexyl-3-thioxoperhydropyrrolo[1,2-c]imidazole-1-one (Compound 35), 2-Phenyl-2,5,6,7,7a-pentahydro-2-azapyrrolizine-1,3-dione (Compound 36), and 2-phenyl-3-thioxo-2,5,6,7,7a-pentahydro-2-azapyrrolizin-1-one (Compound 37).

TABLE II (II)

| No. | $X_1$ | $X_2$ | D | R |
|---|---|---|---|---|
| 38 | O | O | methyl | Phenyl |
| 39 | S | O | methyl | Phenyl |
| 40 | S | O | ethyl | Phenyl |
| 41 | O | O | heptyl | Hydrogen |
| 42 | O | O | octyl | Hydrogen |
| 43 | S | O | propyl | Phenyl |
| 44 | O | O | hexyl | Hydrogen |
| 45 | O | O | bond | Cyclohexyl |
| 46 | O | O | ethyl | Phenyl |
| 47 | S | O | heptyl | Hydrogen |
| 48 | O | O | octyl | Hydrogen |
| 49 | S | O | pentyl | 3-Pyridyl |
| 50 | O | O | propyl | Phenyl |
| 51 | O | O | bond | 3-(Phenoxy)phenyl |
| 52 | O | O | bond | 4-(tert-butyl)phenyl |
| 53 | O | O | bond | 2-(Prop-2-enyl)phenyl |
| 54 | O | O | bond | 3-(Ethoxy)phenyl |
| 55 | S | O | bond | Cyclopentyl |
| 56 | S | O | bond | Quinolinyl |
| 57 | O | O | hexyl | Phenyl |
| 58 | O | O | ethyl | Phenyl |
| 59 | O | O | bond | Cyclopentyl |
| 60 | S | S | bond | 2-thienyl |
| 61 | O | S | bond | 2-thienyl |
| 62 | O | NH | bond | 2-oxazolyl |
| 63 | S | O | bond | 2-furyl |
| 64 | O | O | bond | 3-furyl |
| 65 | S | NH | hexyl | 4-furyl |
| 66 | O | N—CN | bond | Adamantyl |
| 67 | S | N—$NO_2$ | bond | Carbazole |
| 68 | O | S | bond | Adamantyl |
| 69 | S | $NC_3H_7$ | bond | 2-Pyrazolyl |
| 70 | NOH | O | hexyl | Hydrogen |
| 71 | $NOCH_3$ | O | bond | Cyclopentyl |
| 72 | O | O | bond | Phenyl |
| 73 | S | O | bond | Phenyl |
| 74 | O | O | butyl | Hydrogen |

Preferred compounds of TABLE II are named as follows:

2-Benzyl-2,5,6,7,8,8a-hexahydro-2-azaindolizine-1,3-dione (Compound 38), 2-benzyl-3-thioxo-2,5,6,7,8,8a-hexahydro-2-azaindolizin-1-one (Compound 39), 2-(2-phenylethyl)-3-thioxo-2,5,6,7,8,8a-hexahydro-2-azaindolizin-1-one (Compound 40), 2-Heptyl-2,5,6,7,8,8a-hexahydro-2-azaindolizine-1,3-dione (Compound 41), 2-Octyl-2,5,6,7,8,8a-hexahydro-2-azaindolizine-1,3-dione (Compound 42), 2-(3-phenylpropyl)-3-thioxo-2,5,6,7,8,8a-hexahydro-2-azaindolizin-1-one (Compound 43), 2-hexyl-2,5,6,7,8,8a-hexahydro-2-azaindolizine-1,3-dione (Compound 44), 2-Cyclohexyl-2,5,6,7,8,8a-hexahydro-2-azaindolizine-1,3-dione (Compound 45), 2-phenyl-2,5,6,7,8,8a-hexahydro-2-azaindolizine-1,3-dione (Compound 72), 2-phenyl-3-thioxo-2,5,6,7,8,8a-hexahydro-2-azaindolizin-1-one (Compound 73), and 2-butyl-2,5,6,7,8,8a-hexahydro-2-azaindolizine-1,3-dione (Compound 74).

Other compounds which are hydantoin derivative compounds within the scope of the present invention are those compounds which may possess immunosuppressive, non-immunosuppressive, or other activities as long as they also are useful in treating a disease. In particular, other hydantoin derivative compounds falling within the scope of the present invention are useful for preventing and/or treating neurological disorders, including physically damaged nerves and neurodegenerative diseases; in treating alopecia and promoting hair growth; in treating vision disorders and/or improving vision; in treating memory impairment and/or enhancing memory performance; and/or in treating sensorineural hearing loss.

Pharmaceutical Compositions of the Present Invention

The present invention relates to a pharmaceutical composition comprising:

(i) an effective amount of a hydantoin derivative compound of formulae III or IV; and (ii) a pharmaceutically acceptable carrier.

The present invention also relates to a pharmaceutical composition comprising:

(i) an effective amount of a hydantoin derivative compound of formulae III or IV for treating neurodegenerative diseases, neurological disorders, and nerve damage, or promoting nerve growth in animals; and (ii) a pharmaceutically acceptable carrier.

The present invention also relates to a pharmaceutical composition comprising:

(i) an effective amount of a hydantoin derivative compound of formulae III or IV for treating alopecia or promoting hair growth in an animal; and (ii) a pharmaceutically acceptable carrier.

The present invention also relates to a pharmaceutical composition comprising:

(i) an effective amount of a hydantoin derivative compound of formulae III or IV for treating a vision disorder, improving vision, treating memory impairment, or enhancing memory performance in an animal; and (ii) a pharmaceutically acceptable carrier.

The present invention also relates to a pharmaceutical composition comprising:

(i) an effective amount of a hydantoin derivative compound of formulae III or IV for treating sensorineural hearing loss in an animal; and (ii) a pharmaceutically acceptable carrier.

In another preferred embodiment, the novel compounds of the present invention can be administered in pharmaceutical compositions additionally containing other neurotrophic agents such as neurotrophic growth factor, brain derived growth factor, glial derived growth factor, cilial neurotrophic factor, insulin growth factor and active truncated derivatives thereof, acidic fibroblast growth factor, basic fibroblast growth factor, platelet-derived growth factors, neurotropin-3 and neurotropin 4/5. The dosage level of other neurotrophic drugs will depend upon the factors previously stated and the neurotrophic effectiveness of the drug combination.

Methods of the Present Invention

The present invention relates to the use of any of the compounds seen in Tables III and IV, any of the other compounds described above, and other compounds not specifically mentioned or described herein, in the preparation of a medicament for the treatment of a disease. In a preferred embodiment, the disease to be treated includes peripheral neuropathy caused by physical injury or disease state, physical damage to the brain, physical damage to the spinal cord, stroke associated with brain damage, Alzheimer's Disease, Parkinson's Disease, amyotrophic lateral sclerosis, and Huntington's Disease.

The present invention also relates to the use of any of the hydantoin derivative compounds described herein for the treatment of a disease. In particular, the disease to be treated includes the above-mentioned neuropathies, neurological disorders, and neurological damage.

The present invention also relates to a method for treating alopecia or promoting hair growth in an animal, which comprises administering to said animal an effective amount of a hydantoin derivative compound. The present invention also relates to using the inventive compounds and compositions in the preparation of a medicament for the treatment of alopecia or promoting hair growth in an animal.

The inventive method is particularly useful for treating male pattern alopecia, alopecia senilis, alopecia areata, alopecia resulting from skin lesions or tumors, alopecia resulting from cancer therapy such as chemotherapy and radiation, and alopecia resulting from systematic disorders such as nutritional disorders and internal secretion disorders.

The present invention also relates to a method for treating a vision disorder, improving vision, treating memory impairment, or enhancing memory performance in an animal, which comprises administering to said animal an effective amount of a hydantoin derivative compound. The present invention also relates to using the inventive compounds and compositions in the preparation of a medicament for the treatment of a vision disorder, improving vision, treating memory impairment, or enhancing memory performance.

The inventive methods are particularly useful for treating various eye disorders including, but not limited to visual disorders, diseases, injuries, and complications, genetic disorders; disorders associated with aging or degenerative vision diseases; vision disorders correlating to physical injury to the eye, head, or other parts of the body resulting from external forces; disorders resulting from environmental factors; disorders resulting from a broad range of diseases; and combinations of any of the above.

In particular, the compositions and methods of the present invention are useful for improving vision, or correcting, treating, or preventing visual (ocular) impairment or dysfunction of the visual system, including permanent and temporary visual impairment, without limitation. The present invention is also useful in preventing and treating ophthalmologic diseases and disorders, treating damaged and injured eyes, and preventing and treating diseases, disorders, and injuries which result in vision deficiency, vision loss, or reduced capacity to see or process images, and the symptoms and complications resulting from same. The eye diseases and disorders which may be treated or prevented by the compositions and methods of the present invention are not limited with regard to the cause of said diseases or disorders. Accordingly, said compositions and methods are applicable whether the disease or disorder is caused by genetic or environmental factors, as well as any other influences. The compositions and methods of the present invention are particularly useful for eye problems or vision loss or deficiency associated with all of the following, without limitation: aging, cellular or physiological degeneration, central nervous system or neurological disorder, vascular defects, muscular defects, and exposure to adverse environmental conditions or substances.

The compositions and methods of the present invention are particularly useful in correcting, treating, or improving visual impairment, without limitation. Visual impairment in varying degrees occurs in the presence of a deviation from normal in one or more functions of the eye, including (1) visual acuity for objects at distance and near; (2) visual fields; and (3) ocular motility without diplopia. See *Physicians' Desk Reference (PDR) for Ophthalmology*, 16th Edition, 6:47 (1988). Vision is imperfect without the coordinated function of all three. Id.

Said compositions and methods of use are also useful in correcting, treating, or improving other ocular functions including, without limitation, color perception, adaptation to light and dark, accommodation, metamorphopsia, and binocular vision. The compositions and methods of use are particularly useful in treating, correcting, or preventing ocular disturbances including, without limitation, paresis of accommodation, iridoplegia, entropion, ectropion, epiphora, lagophthalmos, scarring, vitreous opacities, non-reactive pupil, light scattering disturbances of the cornea or other media, and permanent deformities of the orbit.

The compositions and methods of use of the present invention are also highly useful in improving vision and treating vision loss. Vision loss ranging from slight loss to absolute loss may be treated or prevented using said compositions and methods of use. Vision may be improved by the treatment of eye disorders, diseases, and injuries using the compositions and methods of the invention. However, improvements in vision using the compositions and methods of use are not so limited, and may occur in the absence of any such disorder, disease, or injury.

The present invention also relates to a method for treating a sensorineural hearing loss in an animal, which comprises administering to said animal an effective amount of a hydantoin derivative compound. The present invention also relates to using the inventive compounds and compositions in the preparation of a medicament for the treatment of sensorineural hearing loss.

It is further contemplated that administration of an inventive compound will protect hair cells and spiral ganglion neurons from traumatic damage, for example damage caused by noise trauma, acute or chronic treatment with cisplatin and aminoglycoside antibiotics of from damage resulting from a lack of neurotrophic factors resulting from interruption of transport of the factors from the axon to the cell body. Such treatment is expected to allow hair cells and/or auditory neurons to tolerate intermittent insults from either environmental noise trauma or treatment with ototoxins, and to slow down, prevent or reverse the progressive degeneration of the auditory neurons and hair cells which is responsible for hearing loss in pathological conditions such as presbycusis (age-related hearing loss), inherited sensorineural degeneration, and post-idiopathic hearing losses and to preserve the functional integrity of the inner ear. Such treatment will also support the auditory neurons for better and longer performance of cochlear implants.

It is understood, however, that a specific dose level for any particular patient will depend upon a variety of factors including the activity of the specific compound employed, the age, body weight, general health, sex, diet, time of administration, rate of excretion, drug combination, and the severity of the particular disease or disorder being treated and form of administration.

$K_i$ Test Procedure

The binding to FBKP12 and inhibition of the peptidyl-prolyl isomerase (rotamase) activity of the compounds used in the inventive methods and pharmaceutical compositions can be evaluated by known methods described in the literature (Harding et al., *Nature*, 1989, 341:758–760; Holt et al. *J. Am. Chem. Soc.*, 115:9923–9938). These values are obtained as apparent $K_i$'s and are presented for representative compounds in TABLE III.

The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent $K_1$ values.

In a plastic cuvette are added 950 mL of ice cold assay buffer (25 mM HEPES, pH 7.8, 100 mM NaCl), 10 mL of FKBP (2.5 mM in 10 mM Tris-Cl pH 7.5, 100 mM NaCl, 1 mM dithiothreitol), 25 mL of chymotrypsin (50 mg/ml in 1 mM HCl) and 10 mL of test compound at various concentrations in dimethyl sulfoxide. The reaction is initiated by the addition of 5 mL of substrate (succinyl-Ala-Phe-Pro-Phe-para-nitroanilide, 5 mg/mL in 2.35 mM LiCl in trifluoroethanol).

The absorbance at 390 nm versus time is monitored for 90 seconds using a spectrophotometer and the rate constants are determined from the absorbance versus time data files.

TABLE III

In Vitro Test Results

| Compound | $K_i$ (nM) |
|---|---|
| 1 | >10,000 |
| 6 | >5,000 |
| 35 | >10,000 |

MPTP Model of Parkinson's Disease in Mice

MPTP lesioning of dopaminergic neurons in mice was used as an animal model of Parkinson's Disease. Four week old male CD1 white mice were dosed i.p. with 30 mg/kg of MPTP for 5 days. Inventive compounds (4 mg/kg), or vehicle, were administered s.c. along with the MPTP for 5 days, as well as for an additional 5 days following cessation of MPTP treatment (Table IV). Inventive compounds (10 mg/kg), or vehicle, were also administered p.o. along with the MPTP for 5 days, as well as for an additional 5 days following cessation of MPTP treatment (Table V). At 18 days following MPTP treatment, the animals were sacrificed and the striata were dissected and homogenized. Immunostaining was performed on saggital and coronal brain sections using anti-tyrosine hydoxylase Ig to quantitate survival and recovery of dopaminergic neurons. In animals treated with MPTP and vehicle, a substantial loss of functional dopaminergic terminals was observed as compared to non-lesioned animals. In another protocol, test compounds were administered only subsequent to MPTP-induced lesioning. Thus, after animals were treated with MPTP for 5 days, an additional 3 days passed before beginning oral drug treatment on day 8. Animals were treated with inventive compounds (0.4 mg/kg), administered orally, once a day for 5 days total. On day 18, the animals were sacrificed and analyzed as described above. Tables IV and V present the percent recovery of dopaminergic neurons in the first (concurrent dosing) paradigms in animals receiving hydantoin derivative compounds.

Tables IV and V, below, show the remarkable neuroregenerative effects of the inventive hydantoin derivative compounds illustrating the neurotrophic capability of these compounds as a class showing that lesioned animals receiving the hydantoin derivative compounds provide a remarkable recovery of TH-stained dopaminergic neurons.

TABLE IV

| | % Recovery |
|---|---|
| Compound 1 | 32.20% |

TABLE V

| | % Recovery |
|---|---|
| Compound 2 | 38.40% |
| Compound 3 | 78.80% |
| Compound 4 | 49.30% |
| Compound 7 | 37.50% |
| Compound 8 | 42.50% |
| Compound 35 | 24.40% |
| Compound 38 | 31.40% |
| Compound 39 | 11.20% |
| Compound 40 | 11.00% |
| Compound 41 | 8.80% |
| Compound 42 | 17.40% |
| Compound 43 | 40.10% |
| Compound 72 | 37.20% |
| Compound 74 | 46.40% |

Percent striatal innervation density was quantitated in brain sections with an anti-tyrosine hydroxylase immunoglobulin, which is indicative of functional dopaminergic neurons. The striatal innervation density of 23% for animals pretreated with only a vehicle and administered a vehicle orally during treatment, is indicative of normal non-lesioned striatal tissue. Striatal innervation density is reduced to 5% for animals pretreated with MPTP and administered a vehicle orally during treatment, and is indicative of MPTP-induced lesioning. Surprisingly, striatal innervation density is increased 8–13% for animals pretreated with MPTP and administered 0.4 mg/kg orally during treatment, indicating substantial neuronal regeneration after induction of MPTP-derived lesions.

Synthesis of Compounds of the Invention

The compounds for use in the methods and compositions of the invention may be readily prepared by standard techniques of organic chemistry, utilizing the general synthetic pathways depicted below.

In the preparation of the compounds of the invention, one skilled in the art will understand that one may need to protect or block various reactive functionalities on the starting compounds or intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to "Protective Groups in Organic Chemistry," McOmie, ed., Plenum Press, New York, N.Y.; and "Protective Groups in Organic Synthesis," Greene, ed., John Wiley & Sons, New York, N.Y. (1981) for the teaching of protective groups which may be useful in the preparation of compounds of the present invention.

The product and intermediates may be isolated or purified using one or more standard purification techniques, including, for example, one or more of simple solvent evaporation, recrystallization, distillation, sublimation, filtration, chromatography, including thin-layer chromatography, HPLC (e.g. reverse phase HPLC), column chromatography, flash chromatography, radial chromatography, trituration, and the like.

The compounds of the present invention may be prepared by reacting amino acids with isocyanates and isothiocyanates, as shown in the general method of Scheme I:

Scheme I

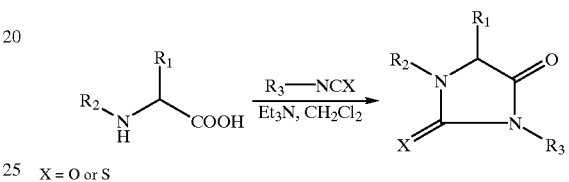

X = O or S

EXAMPLES

The following examples are illustrative of the present invention and are not intended to be limitations thereon. Unless otherwise indicated, all percentages are based upon 100% by weight of the final composition.

Example 1

Synthesis of 2-phenyl-2,5,6,7,8,8a-hexahydro-2-azaindolizine-1,3-dione

A solution of L-pipecolic acid methyl ester (1.0 g; 3.58 mmol), phenylisocyanate (0.42 ml; 3.93 mmol), and triethylamine (1.64 ml; 11.8 mmol) in methylene chloride (15 ml) was stirred overnight at room temperature. The solvent was removed under vacuum, the residue was dissolved in 50 ml of 50% ethyl acetate in hexane, and the organic phase was washed with water and brine, dried, and concentrated. The residue was purified on a flash column, eluting with 40% ethyl acetate in hexane, to obtain the product as a white solid, $^1$H NMR (MeOH, 400 MHz): δ 1.47–1.57 (cm, 3H); 1.62 (bd, 1H, J=9.99); 2.01 (bd, 1H, J=10.36); 2.20 (bd, 1H, J=9.88); 2.96 (t, 1H, J=9.35); 4.06–4.17 (m, 2H); 7.35–7.40 (m, 3H); 7.45–7.48 (m, 2H). Anal. Calcd. for: C, 67.81; H, 6.13; N, 12.17. Found: C, 67.93; H, 6.15; N, 12.21. Mp=186.1–186.7° C.

Example 2

Synthesis of 2-(2-phenylethyl)-3-thioxo-2,5,6,7,7a-pentahydro-2-azapyrrolizin-1-one A solution of L-proline methyl ester (1.0 g; 6.03 mmol), phenethylisothiocyanate (1.08 ml; 6.63 mmol), and triethylamine (2 ml; 15.07 mmol) in 15 ml of methylene chloride was stirred overnight at room temperature. The reaction was worked up as described previously, and the product purified to deliver a white solid, $^1$H NMR (CDCl$_3$, 400 MHz): δ 1.56–1.62 (m, 1H); 2.10–2.26 (m, 3H); 2.96–3.01 (m, 2H); 3.52–3.58 (m, 1H); 3.92–3.99 (m, 3H); 4.00–4.12 (m, 1H);

7.19–7.31 (m, 5H). Anal. Calcd. for: C, 64.59; H, 6.19; N, 10.76; S, 12.32. Found: C, 64.69; H, 6.13; N, 10.71; S, 12.44. Mp=61.2–63.5° C.

Example 3

2-(3-phenylpropyl)-3-thioxo-2,5,6,7,7a-pentahydro-2-azapyrrolizin-1-one

This example was prepared according to the method previously described. $^1$H NMR (CDCl$_3$, 400 MHz): δ 1.60–1.63 (m, 1H); 2.00–2.06 (m, 2H); 2.12–2.18 (m, 1H); 2.20–2.26 (m, 2H); 2.66 (t, 2H, J=7.65); 3.51–3.57 (m, 1H); 3.80–3.85 (m, 2H); 3.90–3.97 (m, 1H); 4.07–4.12 (m, 1H); 7.15–7.25 (m, 5H). Anal. Calcd. for: C, 65.66; H, 6.61; N, 10.21; S, 11.69. Found: C, 65.66; H, 6.56; N, 10.14; S, 11.71.

Example 4

(7aS)-2-Cyclohexyl-3-thioxoperhydropyrrolo[1,2-c]imidazole-1-one

This example was prepared according to the method previously described. $^1$H NMR (CDCl$_3$, 400 MHz): δ 1.12–1.41 (m, 3H); 1.59–1.65 (m, 4H); 1.69–1.81 (m, 2H); 2.10–2.21 (m, 2H); 2.25–2.38 (m, 3H); 3.61–3.66 (m, 1H); 3.90–3.98 (m, 1H); 4.02–4.13 (m, 1H); 4.44–4.51 (m, 1H). Anal. Calcd. for C$_{12}$H$_{18}$N$_2$OS: C, 60.47; H, 7.61; N, 11.75; S, 13.45. Found: C, 60.52; H, 7.60; N, 11.73; S, 13.27.

Example 5

(7aS)-2-(2'-Phenyl)phenylperhydropyrrolo[1,2-c]imidazole-1,3-dione

This example was prepared according to the method previously described. $^1$H NMR (CDCl$_3$, 400 MHz): δ 1.00–1.16 (m, 1H); 1.58–2.25 (cm, 3H); 3.12–3.22 (m, 1H); 3.57–3.72 (m, 1H); 3.92–4.04 (m, 1H); 7.20–7.52 (m, 9H). Anal. Calcd. for C$_{18}$H$_{16}$N$_2$O$_2$0.05 EtOAc: C, 73.67; H, 5.57; N, 9.44. Found: C, 73.50; H, 5.87; N, 9.74.

Example 6

(7aS)-2-(4-(Trifluoromethyl)phenyl]perhydropyrrolo[1,2-c]imidazole-1,3-dione

This example was prepared according to the method previously described. $^1$H NMR (CDCl$_3$, 400 MHz): δ 1.82–1.99 (m, 1H); 2.14–2.22 (m, 2H); 2.34–2.39 (m, 1H); 3.34–3.40 (m, 1H); 3.77–3.84 (m, 1H); 4.24–4.29 (m, 1H); 7.67 (d, 2H, J=8.35); 7.72 (d, 2H, J=8.60). Anal. Calcd. for C$_{13}$H$_{11}$N$_2$O$_2$F: C, 54.93; H, 3.90; N, 9.86. Found: C, 55.45; H, 4.26; N, 9.87.

Example 7

(7aS)-2-(1-Naphthyl)perhydropyrrolo[1,2-c]imidazole-1,3-dione

This example was prepared according to the method previously described. $^1$H NMR (CDCl$_3$, 300 MHz): δ 1.94–2.03 (m, 1H); 2.05–2.33 (m, 2H); 2.39–2.51 (m, 1H); 3.38–3.44 (m, 1H); 3.83–4.09 (m, 1H); 4.41 (dt, 1H, J=7.45); 7.38–7.96 (m, 2H). Anal. Calcd. for C$_{16}$H$_{14}$N$_2$O$_2$: C, 72.17; H, 5.30; N, 10.52. Found: C, 72.05; H, 5.32; N, 10.51.

Example 8

2-Phenyl-2,5,6,7,7a-pentahydro-2-azapyrrolizine-1,3-dione

This example was prepared according to the method previously described. $^1$H NMR (CDCl$_3$, 400 MHz): δ 1.78 (m, 1H); 2.10 (m, 2H); 2.26 (m, 1H); 3.28 (m, 1H); 3.73 (q, 1H); 4.17 (t, 2H); 7.31 (m, 3H); 7.38 (m, 2H).

Example 9

2-benzyl-2 5,6,7,8,8a-hexahydro-2-azaindolizine-1,3-dione

This example was prepared according to the method previously described. $^1$H NMR (MeOH, 400 MHz): δ 1.26–1.39 (m, 2H); 1.50–1.57 (m, 1H); 1.7 (bd, 1H, J=10.03); 1.95 (bd, 1H, J=13.56); 2.13 (bd, 1H, J=9.57); 2.89 (td, 1H, J=9.44, 3.52); 3.93 (dd, 1H, j=12.07, 4.26); 4.04–4.09 (m, 1H); 4.61 (s, 2H); 7.24–7.31 (m, 5H). Anal. Calcd. for: C, 68.83; H, 6.60; N, 11.47. Found: C, 68.90; H, 6.61; N, 11.48.

Example 10

2-benzyl-3-thioxo-2,5,6,7,7a-pentahydro-2-azapyrrolizin-1-one

This example was prepared according to the method previously described. $^1$H NMR (MeOH, 400 MHz): δ 1.60–1.66 (m, 1H); 2.20–2.26 (m, 3H); 3.50–3.56 (m, 1H); 3.86–3.93 (m, 1H); 4.33–4.37 (m, 1H); 4.95 (d, 2H, J=14.81); 7.20–7.29 (m, 3H); 7.30–7.37 (m, 2H). Anal. Calcd. for: C, 63.39; H, 5.73; N, 11.37; S, 13.02. Found: C, 63.60; H, 5.90; N, 11.21; S, 12.92.

Example 11

2-benzyl-3-thioxo-2,5,6,7,8,8a-hexahydro-2-azaindolizin-1-one

This example was prepared according to the method previously described. $^1$H NMR (MeOH, 400 MHz): δ 1.30–1.33 (m, 1H); 1.42–1.45 (m, 1H); 1.69 (q, 1H, J=9.55); 1.82 (bd, 1H, J=13.38); 1.95 (bd, 1H, J=13.55); 2.16 (bd, 1H, J=12.91); 3.09 (td, 1H, J=3.27, 13.11); 4.07 (dd, 1H, J=7.18, 4.13); 4.76 (dd, 1H, J=9.46, 3.46); 4.97 (d, 2H); 7.22–7.29 (m, 3H); 7.36–7.38 (m, 2H). Anal. Calcd. for: C, 64.59; H, 6.19; N, 10.76; S, 12.32. Found: C, 64.69; H, 6.22; N, 10.83; S, 12.32.

Example 12

2-(2-phenylethyl)-3-thioxo-2,5,6,7,8,8a-hexahydro-2-azaindolizin-1-one

This example was prepared according to the method previously described. $^1$H NMR (CDCl$_3$, 400 MHz): δ 1.22–1.26 (m, 1H); 1.44–1.49 (m, 2H); 1.82 (bd, 1H, J=10.00); 1.95 (bd, 1H, J=11.04); 2.18 (bd, 1H, J=10.11); 2.95–3.03 (m, 3H); 3.76 (dd, 1H, J=4.34, 12.14); 4.01–4.06 (m, 2H); 4.83 (bd, 1H, J=13.32); 7.19–7.29 (m, 5H). Anal. Calcd. -with 0.20 H$_2$O for: C, 64.81; H, 6.67; N, 10.08; S, 11.53. Found: C, 64.64; H, 6.60; N, 9.92; S, 11.57.

Example 13

2-heptyl-2,5,6,7,8,8a-hexahydro-2-azaindolizine-1,3-dione

This example was prepared according to the method previously described. $^1$H NMR (MeOH, 400 MHz): δ 0.87–0.91 (m, 4H); 1.30 (bs, 9H); 1.53–1.59 (m, 3H); 1.73 (bd, 1H, J=13.17); 1.94 (bd, 1H, J=10.43); 2.13 (bd, 1H, J=12.69); 2.88 (td, 1H, J=3.50, 9.57); 3.30 (s, 1H); 3.43–3.47 (m, 1H); 3.89 (dd, 1H, J=4.20, 11.94); 4.06 (dd, 1H, J=3.85, 12.85). Anal. Calcd. for: C, 66.63; H, 9.59; N, 11.10. Found: C, 66.37; H, 9.56; N, 10.99.

Example 14

2-octyl-2,5,6,7,8,8a-hexahydro-2-azaindolizine-1,3-dione

This example was prepared according to the method previously described. $^1$H NMR (CDCl$_3$, 400 MHz): δ 0.87 (bs, 3H); 1.28 (bs, 11H); 1.36–1.50 (m, 2H); 1.59 (bs, 2H); 1.97 (bd, 1H, J=11.28); 2.18 (bd, 1H, J=13.16); 2.22 (bd, 1H, J=13.12); 2.81 (td, 1H, J=3.45, 12.86); 3.47 (t, 2H, J=7.39); 3.72 (dd, 1H, J=4.24, 11.96); 4.17 (dd, 1H, J=4.71, 13.31). Anal. Calcd. for: C, 67.63; H, 9.84; N, 10.52. Found: C, 67.89; H, 10.01; N, 10.42.

Example 15

2-phenyl-3-thioxo-2 5,6,7,8,8a-hexahydro-2-azaindolizin-1-one

This example was prepared according to the method previously described. $^1$H NMR (MeOH, 400 MHz): δ 1.54–1.66 (m, 3H); 1.88 (bd, 1H, J=8.49); 1.90–2.08 (m, 1H); 2.35 (bd, 1H, J=11.96); 3.10 (td, 1H, J=3.68, 12.85); 4.04 (dd, 1H, J=4.48, 11.67); 4.93 (dd, 1H, J=1.95, 11.03); 7.30–7.32 (m, 2H); 7.41–7.51 (m, 3H). Anal. Calcd. for: C, 63.39; H, 5.73; N, 11.37; S, 13.02. Found: C, 63.53; H, 5.82; N, 11.32; S, 13.07.

Example 16

2-(3-phenylpropyl)-3-thioxo-2, 5,6,7,8,8a-hexahydro-2-azaindolizin-1-one

This example was prepared according to the method previously described. $^1$H NMR (CDCl$_3$, 400 MHz): δ 1.23–1.29 (m, 2H); 1.47–1.54 (m, 2H); 1.79 (bd, 1H, J=10.18); 1.82–2.08 (m, 2H); 2.22 (bd, 1H, J=13.02); 2.67 (t, 2H, J=7.61); 2.95 (td, 1H, J=3.33, 9.59); 3.71 (dd, 1H, J=4.31, 12.14); 3.85–3.89 (m, 2H); 4.82 (dd, 1H, J=4.45, 13.18); 7.14–7.28 (m, 5H). Anal. Calcd. for: C, 66.63; H, 6.99; N, 9.71; S, 11.12. Found: C, 66.75; H, 7.08; N, 9.67; S, 11.21.

Example 17

2-butyl-2,5,6,7,8,8a-hexahydro-2-azaindolizine-1,3-dione

This example was prepared according to the method previously described. $^1$H NMR (CDCl$_3$, 400 MHz): δ 0.92 (t, 3H, J=7.33); 1.24–1.63 (cm, 7H); 1.73 (bd, 1H, J=8.55); 1.98 (bd, 1H, J=13.44); 2.21 (bd, 1H, J=9.90); 2.81 (td, 1H, J=3.56, 12.78); 3.49 (t, 2H, J=7.34); 3.72 (dd, 1H, J=4.26, 11.97); 4.15 (dd, 1H, J=4.74, 13.33). Anal. Calcd. for: C, 62.83; H, 8.63; N, 13.32. Found: C, 62.57; H, 8.54; N, 13.17.

Example 18

2-hexyl-2,5,6,7,8,8a-hexahydro-2-azaindolizine-1,3-dione

This example was prepared according to the method previously described. $^1$H NMR (MeOH, 400 MHz): δ 0.88–0.91 (m, 3H); 1.25–1.34 (bs, 8H); 1.50–1.58 (m, 3H); 1.71–1.75 (m, 1H); 1.92–1.96 (m, 1H); 2.11–2.15 (m, 1H); 2.85–2.93 (m, 1H); 3.43–3.47 (m, 2H); 3.87–3.91 (m, 1H); 4.04–4.08 (m, 1H). Anal. Calcd. with 0.1 EtOAc for: C, 65.12; H, 9.30; N, 11.34. Found: C, 64.87; H, 9.26; N, 11.54.

Example 19

2-hexyl-2,5,6,7,7a-pentahydro-2-azapyrrolizine-1,3-dione

This example was prepared according to the method previously described. $^1$H NMR (CDCl$_3$, 400 MHz): δ 0.85–0.89 (bs, 3H); 1.28 (bs, 7H); 1.59 (m, 1H); 1.63–1.73 (m, 1H); 2.22–2.24 (m, 2H); 2.25–2.27 (m, 1H); 3.21–3.27 (m, 1H); 3.43–3.47 (m, 2H); 3.65–3.72 (m, 1H); 4.06 (dd, 1H, J=1.20, 7.22). Anal. Calcd. for: C, 64.26; H, 8.99; N, 12.49. Found: C, 64.02; H, 9.00; N, 12.42.

Example 20

2-phenyl-3-thioxo-2,5,6,7,7a-pentahydro-2-azapyrrolizin-1-one

This example was prepared according to the method previously described. $^1$H NMR (CDCl$_3$, 400 MHz): δ 1.85–1.93 (m, 1H); 2.21–2.27 (m, 1H); 2.31–2.43 (m, 2H); 3.63–3.69 (m, 1H); 4.04–4.11 (m, 1H); 4.38 (dd, 1H, J=6.96, 10.39); 7.25–7.32 (m, 2H); 7.40–7.51 (m, 3H). Mp=187.3–189.7° C. Anal. Calcd. for: C, 62.04; H, 5.21; N, 12.06; S, 13.80. Found: C, 61.85; H, 5.26; N, 12.01; S, 13.97.

Example 21

A lotion comprising the following composition may be prepared.

|  | (%) |
|---|---|
| 95% Ethanol | 80.0 |
| a hydantoin derivative | 10.0 |
| α-Tocopherol acetate | 0.01 |
| Ethylene oxide (40 mole) adducts of hardened castor oil | 0.5 |
| purified water | 9.0 |
| perfume and dye | q.s. |

Into 95% ethanol are added a hydantoin derivative, α-tocopherol acetate, ethylene oxide (40 mole) adducts of hardened castor oil, perfume, and a dye. The resulting mixture is stirred and dissolved, and purified water is added to the mixture to obtain a transparent liquid lotion.

5 ml of the lotion may be applied once or twice per day to a site having marked baldness or alopecia.

Example 22

A lotion comprising the following composition shown may be prepared.

|  | (%) |
|---|---|
| 95% Ethanol | 80.0 |
| a hydantoin derivative | 0.005 |
| Hinokitol | 0.01 |
| Ethylene oxide (40 mole) adducts of hardened castor oil | 0.5 |
| Purified water | 19.0 |
| Perfume and dye | q.s. |

Into 95% ethanol are added a hydantoin derivative, hinokitol, ethylene oxide (40 mole) adducts of hardened castor oil, perfume, and a dye. The resulting mixture is stirred, and purified water is added to the mixture to obtain a transparent liquid lotion.

The lotion may be applied by spraying once to 4 times per day to a site having marked baldness or alopecia.

Example 23

An emulsion may be prepared from A phase and B phase having the following compositions.

|  | (%) |
| --- | --- |
| (A phase) | |
| Whale wax | 0.5 |
| Cetanol | 2.0 |
| Petrolatum | 5.0 |
| Squalane | 10.0 |
| Polyoxyethylene (10 mole) monostearate | 2.0 |
| Sorbitan monooleate | 1.0 |
| a hydantoin derivative | 0.01 |
| (B phase) | |
| Glycerine | 10.0 |
| Purified water | 69.0 |
| Perfume, dye, and preservative | q.s. |

The A phase and the B phase are respectively heated and melted and maintained at 80° C. Both phases are then mixed and cooled under stirring to normal temperature to obtain an emulsion.

The emulsion may be applied by spraying once to four times per day to a site having marked baldness or alopecia.

Example 24

A cream may be prepared from A phase and B phase having the following compositions.

|  | (%) |
| --- | --- |
| (A phase) | |
| Fluid paraffin | 5.0 |
| Cetostearyl alcohol | 5.5 |
| Petrolatum | 5.5 |
| Glycerine monostearate | 33.0 |
| Polyoxyethylene (20 mole) 2-octyldodecyl ether | 3.0 |
| Propylparaben | 0.3 |
| (B Phase) | |
| a hydantoin derivative | 0.8 |
| Glycerine | 7.0 |
| Dipropylene glycol | 20.0 |
| Polyethylene glycol 4000 | 5.0 |
| Sodium Hexametaphosphate | 0.005 |
| Purified water | 44.895 |

The A phase is heated and melted, and maintained at 70° C. The B phase is added into the A phase and the mixture is stirred to obtain an emulsion. The emulsion is then cooled to obtain a cream.

The cream may be applied once to 4 times per day to a site having marked baldness or alopecia.

Example 25

A topical liquid comprising the following composition may be prepared.

|  | (%) |
| --- | --- |
| Polyoxyethylene butyl ether | 20.0 |
| Ethanol | 50.0 |
| a hydantoin derivative | 0.001 |
| Propylene glycol | 5.0 |
| Polyoxyethylene hardened castor oil derivative (ethylene oxide 30 mole adducts) | 0.4 |
| Perfume | q.s. |
| Purified water | q.s. |

Into ethanol are added polyoxypropylene butyl ether, propylene glycol, polyoxyethylene hardened castor oil, a hydantoin derivative, and perfume. The resulting mixture is stirred, and purified water is added to the mixture to obtain a liquid.

The liquid may be applied once to 4 times per day to a site having marked baldness or alopecia.

Example 26

A shampoo comprising the following composition may be prepared.

|  | (%) |
| --- | --- |
| Sodium laurylsulfate | 5.0 |
| Triethanolamine laurylsulfate | 5.0 |
| Betaine lauryldimethylaminoacetate | 6.0 |
| Ethylene glycol distearate | 2.0 |
| Polyethylene glycol | 5.0 |
| a hydantoin derivative | 5.0 |
| Ethanol | 2.0 |
| Perfume | 0.3 |
| Purified water | 69.7 |

Into 69.7 of purified water are added 5.0 g of sodium laurylsulfate, 5.0 g of triethanolamine laurylsulfate, 6.0 g of betaine lauryldimethyl-aminoacetate. Then a mixture obtained by adding 5.0 g of a hydantoin derivative, 5.0 g of polyethylene glycol, and 2.0 g of ethylene glycol distearate to 2.0 g of ethanol, followed by stirring, and 0.3 g of perfume are successively added. The resulting mixture is heated and subsequently cooled to obtain a shampoo.

The shampoo may be used on the scalp once or twice per day.

Example 27

A patient is suffering from alopecia senilis. A hydantoin derivative compound, or a pharmaceutical composition comprising the same, may be administered to the patient. Increased hair growth is expected to occur following treatment.

Example 28

A patient is suffering from male pattern alopecia. A hydantoin derivative compound, or a pharmaceutical composition comprising the same, or a pharmaceutical composition comprising the same may be administered to the patient. Increased hair growth is expected to occur following treatment.

Example 29

A patient is suffering from alopecia areata. A hydantoin derivative compound, or a pharmaceutical composition comprising the same, may be administered to the patient. Increased hair growth is expected to occur following treatment.

Example 30

A patient is suffering from hair loss caused by skin lesions. A hydantoin derivative compound, or a pharmaceutical composition comprising the same, may be administered to the patient. Increased hair growth is expected to occur following treatment.

Example 31

A patient is suffering from hair loss caused by tumors. A hydantoin derivative compound, or a pharmaceutical composition comprising the same, may be administered to the patient. Increased hair growth is expected to occur following treatment.

Example 32

A patient is suffering from hair loss caused by a systematic disorder, such as a nutritional disorder or an internal secretion disorder. A hydantoin derivative compound, or a pharmaceutical composition comprising the same, may be administered to the patient. Increased hair growth is expected to occur following treatment.

Example 33

A patient is suffering from hair loss caused by chemotherapy. A hydantoin derivative compound, or a pharmaceutical composition comprising the same, may be administered to the patient. Increased hair growth is expected to occur following treatment.

Example 34

A patient is suffering from hair loss caused by radiation. A hydantoin derivative compound, or a pharmaceutical composition comprising the same may, be administered to the patient. Increased hair growth is expected to occur following treatment.

Example 35

A patient is suffering from a neurodegenerative disease. A hydantoin derivative compound or a pharmaceutical composition comprising the same is administered. It would be expected that the patient would improve their condition or recover.

Example 36

A patient is suffering from a neurological disorder. A hydantoin derivative compound or pharmaceutical compositions comprising same is administered. It would be expected that the patient would improve their condition or recover.

Example 37

A patient is suffering from stroke. A hydantoin derivative compound or pharmaceutical compositions comprising same is administered. It would be expected that the patient would improve their condition or recover.

Example 38

A patient is suffering from Parkinson's Disease. A hydantoin derivative compound or pharmaceutical compositions comprising same is administered. It would be expected that the patient would improve their condition or recover.

Example 39

A patient is suffering from Alzheimer's Disease. A hydantoin derivative compound or pharmaceutical compositions comprising same is administered. It would be expected that the patient would improve their condition or recover.

Example 40

A patient is suffering from Huntington's Disease. A hydantoin derivative compound or pharmaceutical compositions comprising same is administered. It would be expected that the patient would improve their condition or recover.

Example 41

A patient is suffering from a peripheral neuropathy. A hydantoin derivative compound or pharmaceutical compositions comprising same is administered. It would be expected that the patient would improve their condition or recover.

Example 42

A patient is suffering from amyotrophic lateral sclerosis. A hydantoin derivative compound or pharmaceutical compositions comprising same is administered. It would be expected that the patient would improve their condition or recover.

Example 43

A patient is suffering from a spinal injury. A hydantoin derivative compound or pharmaceutical compositions comprising same is administered. It would be expected that the patient would improve their condition or recover.

Example 44

A patient is at risk of suffering from a neurodegenerative disease or neurological disorder. A hydantoin derivative compound or a pharmaceutical composition comprising the same is prophelactically administered. It would be expected that the patient would be prevented from some or all of the effects of the disease or disorder, or would significantly improve their condition or recover over patients who were not pre-treated.

Example 45

A patient is suffering from macular degeneration. A hydantoin derivative compound as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 46

A patient is suffering from glaucoma, resulting in cupping of the optic nerve disc and damage to nerve fibers. A hydantoin derivative compound as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 47

A patient is suffering from cataracts requiring surgery. Following surgery, a hydantoin derivative compound as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 48

A patient is suffering from an impairment or blockage of retinal blood supply relating to diabetic retinopathy, ischemic optic neuropathy, or retinal artery or vein blockage. A hydantoin derivative compound as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 49

A patient is suffering from a detached retina. A hydantoin derivative compound as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 50

A patient is suffering from tissue damage caused by inflammation associated with uveitis or conjunctivitis. A hydantoin derivative compound as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 51

A patient is suffering from photoreceptor damage caused by chronic or acute exposure to ultraviolet light. A hydantoin derivative compound as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 52

A patient is suffering from optic neuritis. A hydantoin derivative compound as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 53

A patient is suffering from tissue damage associated with a "dry eye" disorder. A hydantoin derivative compound as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 54

A patient is suffering from sensorineural hearing loss. A hydantoin derivative compound as identified above, alone or in combination with one or more other factors, or a pharmaceutical composition comprising the same, may be administered to the patient. A reduction in hearing loss is expected to occur following treatment.

The invention being thus described, it will be obvious that the same may be varied in many ways. Such variations are not to be regarded as a departure from the spirit and scope of the invention and all such modifications are intended to be included within the scope of the following claims.

I claim:

1. A pharmaceutical composition comprising
   (i) an effective amount of a compound of the formula:

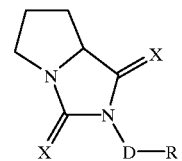

where
   each X independently is O, S, or $NR_2$;
   $R_2$ is selected from the group consisting of cyano, nitro, hydrogen, $C_1$–$C_4$ alkyl,
   hydroxy, and $C_1$–$C_4$ alkoxy;
   D is a direct bond or $C_1$–$C_8$ alkyl or alkenyl;
   R is an alicyclic or aromatic, mono-, bi- or tricyclic, carbo- or heterocyclic ring, wherein when R is an alicyclic monocyclic heterocyclic ring containing a nitrogen heteroatom, the alicyclic monocyclic heterocyclic ring contains only one nitrogen heteroatom;
   wherein R is optionally substituted with one substituent selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenyl, phenoxy, benzyloxy, and amino;
   or a pharmaceutically acceptable salt, ester, or solvate thereof;
   (ii) an additional neurotrophic factor; and
   (iii) a pharmaceutically acceptable carrier.

2. The pharmaceutical composition of claim 1, wherein the additional neurotrophic factor is selected from the group consisting of neurotrophic growth factor, brain derived growth factor, glial derived growth factor, cilial neurotrophic factor, insulin growth factor, acidic fibroblast growth factor, basic fibroblast growth factor, platelet-derived growth factors, neurotropin-3, and neurotropin-4/5.

3. A pharmaceutical composition comprising
(i) an effective amount of a compound of the formula:

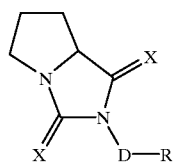

where
   each X independently is O, S, or $NR_2$;
   $R_2$ is selected from the group consisting of cyano, nitro, hydrogen, $C_1$–$C_4$ alkyl, hydroxy, and $C_1$–$C_4$ alkoxy;
   D is a direct bond or $C_1$–$C_4$ alkyl or alkenyl;
   R is hydrogen, or an alicyclic or aromatic, mono-, bi- or tricyclic, carbo- or heterocyclic ring, wherein when R is an alicyclic monocyclic heterocyclic ring containing a nitrogen heteroatom, the alicyclic monocyclic heterocyclic ring contains only one nitrogen heteroatom;
   wherein R is optionally substituted with one substituent selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenyl, phenoxy, benzyloxy, and amino;
   wherein when both X substituents are O and D is a bond, R is not phenyl;
   wherein when one X is O and the other is S and D is a bond, then R is not phenyl;
   wherein when both X substituents are O and R is H, D is not $C_1$–$C_8$ alkyl;

or a pharmaceutically acceptable salt, ester, or solvate thereof;

(ii) an additional neurotrophic factor other than said compound; and (iii) a pharmaceutically acceptable carrier.

* * * * *